US008419722B2

(12) United States Patent
Richards et al.

(10) Patent No.: US 8,419,722 B2
(45) Date of Patent: Apr. 16, 2013

(54) APPARATUS AND METHOD FOR INJECTION OF FIBRIN SEALANT IN SPINAL APPLICATIONS

(75) Inventors: Mark Richards, Leander, TX (US); Brian D. Burkinshaw, Pflugerville, TX (US); Kevin Pauza, Tyler, TX (US); James B. Rogan, Austin, TX (US); John Wheeler, Austin, TX (US)

(73) Assignee: Spinal Restoration, Inc., Austin, TX (US)

( * ) Notice: Subject to any disclaimer, the term of this patent is extended or adjusted under 35 U.S.C. 154(b) by 459 days.

(21) Appl. No.: 11/650,398

(22) Filed: Jan. 5, 2007

(65) Prior Publication Data
US 2007/0191781 A1 Aug. 16, 2007

Related U.S. Application Data

(63) Continuation-in-part of application No. 11/205,760, filed on Aug. 17, 2005, and a continuation-in-part of application No. 11/205,784, filed on Aug. 17, 2005, and a continuation-in-part of application No. 11/205,775, filed on Aug. 17, 2005, now Pat. No. 7,597,687.

(60) Provisional application No. 60/764,020, filed on Feb. 1, 2006, provisional application No. 60/854,413, filed on Oct. 24, 2006, provisional application No. 60/623,600, filed on Oct. 29, 2004.

(51) Int. Cl.
*A61B 18/04* (2006.01)

(52) U.S. Cl.
USPC ............ 606/27; 222/255; 222/280; 222/281; 222/287; 604/48; 604/71; 604/173; 604/191; 604/223; 604/57; 604/58; 604/59; 604/60; 604/61; 604/62; 604/63; 604/64; 604/82; 604/83; 604/84; 604/85; 604/86; 604/87; 604/88; 604/89; 604/90; 604/91; 604/92; 604/181; 604/182; 604/183; 604/184; 604/185; 604/186; 604/187; 604/275; 604/276; 604/277; 604/278; 604/279

(58) Field of Classification Search .............. 222/255, 222/280, 281, 287; 604/48, 71, 173, 191, 604/223, 233, 281, 287, 57–64, 82–92, 181–187, 604/275–279; 433/89, 90
See application file for complete search history.

(56) References Cited

U.S. PATENT DOCUMENTS

| 2,533,004 | A | 12/1950 | Ferry et al. | 260/112 |
| 3,089,815 | A | 5/1963 | Lieb et al. | 167/58 |

(Continued)

FOREIGN PATENT DOCUMENTS

| DE | 3037270 | 5/1982 |
| EP | 0 068 149 | 5/1982 |

(Continued)

OTHER PUBLICATIONS

US 6,645,204, 11/2003, Sharkey et al. (withdrawn).
Abstract: T. Yagita, "Agent for Controlling Formation of Cheloid at Excision Site for Inflammation Bowel Disease" Feb. 10, 1997; Database WPI, Section Ch, Week 199716, Derwent Publications Ltd., London, GB XP002182938.
Abstract: Sumitomo Cement Co., "Sustained Release Agent for Treatment of Osteomyelitis" Jan. 8, 1993; Database WPI, Section Ch, Week 199306, Derwent Publications Ltd., London, GB XP002182939.
G.Y. Bong et al., "Development of Local Antibiotic Delivery System Using Fibrin Glue" Mar. 1, 1996; Journal of Controlled Release, Elsevier Science Publishers, vol. 29, No. 1, pp. 65-70.

(Continued)

*Primary Examiner* — Theodore Stigell
*Assistant Examiner* — Scott Medway
(74) *Attorney, Agent, or Firm* — O'Keefe, Egan, Peterman & Enders LLP

(57) ABSTRACT

An apparatus for percutaneous delivery of a sealant comprising: at least two fluid reservoirs, an introducer needle having a distal tip that is in fluid communication with at least one reservoir, a fluid delivery tube that is in fluid communication with a second reservoir, wherein the fluid delivery tube has a tip and wherein the fluid delivery tube is configured so that the tip of the fluid delivery tube does not extend past the distal tip of the introducer needle during use.

21 Claims, 24 Drawing Sheets

U.S. PATENT DOCUMENTS

| | | | |
|---|---|---|---|
| 4,359,049 A | 11/1982 | Redl et al. | 128/218 PA |
| 4,393,041 A | 7/1983 | Brown et al. | 424/19 |
| 4,427,650 A | 1/1984 | Stroetmann | 424/46 |
| 4,442,655 A | 4/1984 | Stroetmann | 53/428 |
| 4,619,913 A | 10/1986 | Luck et al. | 514/131 |
| RE33,375 E | 10/1990 | Luck et al. | 514/2 |
| 4,979,942 A * | 12/1990 | Wolf et al. | 604/83 |
| 5,080,648 A * | 1/1992 | D'Antonio | 604/72 |
| 5,124,155 A | 6/1992 | Reich | 424/428 |
| 5,264,446 A | 11/1993 | Hegasy et al. | 514/356 |
| 5,290,552 A | 3/1994 | Sierra et al. | 424/94.64 |
| 5,370,273 A * | 12/1994 | Rohloff et al. | 222/132 |
| 5,643,192 A | 7/1997 | Hirsh et al. | 604/4 |
| 5,651,982 A | 7/1997 | Marx | 424/450 |
| 5,702,715 A | 12/1997 | Nikolaychik et al. | 424/402 |
| 5,925,738 A | 7/1999 | Miekka et al. | 530/380 |
| 5,942,241 A | 8/1999 | Chasin et al. | 424/426 |
| 5,962,420 A | 10/1999 | Edwardson et al. | 514/21 |
| 5,980,504 A | 11/1999 | Sharkey et al. | 604/510 |
| 5,980,866 A | 11/1999 | Uchida et al. | 424/45 |
| 6,007,570 A | 12/1999 | Sharkey et al. | 607/96 |
| 6,007,811 A | 12/1999 | Sawyer et al. | 424/94.64 |
| 6,054,122 A | 4/2000 | MacPhee et al. | 424/94.4 |
| 6,073,051 A | 6/2000 | Sharkey et al. | 607/99 |
| 6,079,868 A * | 6/2000 | Rydell | 366/189 |
| 6,095,149 A | 8/2000 | Sharkey et al. | 128/898 |
| 6,117,425 A | 9/2000 | MacPhee et al. | 424/94.64 |
| 6,122,549 A | 9/2000 | Sharkey et al. | 607/99 |
| 6,124,273 A | 9/2000 | Drohan et al. | 514/55 |
| 6,126,682 A | 10/2000 | Sharkey et al. | 607/96 |
| 6,183,518 B1 * | 2/2001 | Ross et al. | 623/17.16 |
| 6,197,325 B1 | 3/2001 | MacPhee et al. | 424/94.64 |
| 6,224,630 B1 | 5/2001 | Bao et al. | 623/17 |
| 6,258,086 B1 | 7/2001 | Ashley et al. | 606/41 |
| 6,261,311 B1 | 7/2001 | Sharkey et al. | 607/96 |
| 6,320,029 B1 | 11/2001 | Miekka et al. | 530/380 |
| 6,428,576 B1 | 8/2002 | Haldimann | 623/17.16 |
| 6,468,527 B2 | 10/2002 | Austin et al. | 424/94.64 |
| 6,503,527 B1 | 1/2003 | Whitmore et al. | 424/422 |
| 6,517,568 B1 | 2/2003 | Sharkey et al. | 607/96 |
| 6,547,810 B1 | 4/2003 | Sharkey et al. | 607/96 |
| 6,554,851 B1 * | 4/2003 | Palasis et al. | 606/213 |
| 6,559,119 B1 | 5/2003 | Burgess et al. | 514/2 |
| 6,565,539 B1 * | 5/2003 | Zinger et al. | 604/191 |
| 6,620,125 B1 * | 9/2003 | Redl | 604/83 |
| 6,638,276 B2 | 10/2003 | Sharkey et al. | 606/41 |
| 6,648,920 B2 | 11/2003 | Ferree | 623/17.11 |
| RE38,431 E | 2/2004 | Miekka et al. | 530/380 |
| 6,695,839 B2 * | 2/2004 | Sharkey et al. | 606/49 |
| 6,726,685 B2 | 4/2004 | To et al. | 606/50 |
| 6,733,472 B1 * | 5/2004 | Epstein et al. | 604/30 |
| 6,733,496 B2 | 5/2004 | Ashley et al. | 606/41 |
| 6,749,605 B2 | 6/2004 | Ashley et al. | 606/41 |
| 6,762,336 B1 | 7/2004 | MacPhee et al. | 602/48 |
| 6,764,467 B1 | 7/2004 | Roby et al. | 604/191 |
| 6,767,347 B2 | 7/2004 | Sharkey et al. | 606/41 |
| 6,780,411 B2 | 8/2004 | Lewis, Jr. et al. | 424/94.64 |
| 6,874,657 B2 * | 4/2005 | Metzner et al. | 222/82 |
| 6,884,232 B1 * | 4/2005 | Hagmann et al. | 604/82 |
| 6,921,532 B1 | 7/2005 | Austin et al. | 424/94.64 |
| 7,004,945 B2 | 2/2006 | Boyd et al. | 606/92 |
| 7,004,971 B2 | 2/2006 | Serhan et al. | 623/17.16 |
| 7,449,019 B2 | 11/2008 | Uchida et al. | 606/27 |
| 7,455,657 B2 * | 11/2008 | Naimark et al. | 604/82 |
| 2002/0045668 A1 | 4/2002 | Dang et al. | 514/649 |
| 2002/0110554 A1 | 8/2002 | Lewis, Jr. et al. | 424/94.64 |
| 2003/0091558 A1 * | 5/2003 | Woolverton | 424/94.64 |
| 2003/0130617 A1 * | 7/2003 | Leone | 604/82 |
| 2003/0181964 A1 | 9/2003 | Sharkey et al. | 607/96 |
| 2004/0092864 A1 * | 5/2004 | Boehm et al. | 604/82 |
| 2004/0111136 A1 | 6/2004 | Sharkey et al. | 607/99 |
| 2004/0191261 A1 | 9/2004 | Redl et al. | 424/178.1 |
| 2004/0192658 A1 | 9/2004 | Hunter et al. | 514/152 |
| 2004/0193151 A1 | 9/2004 | To et al. | 606/41 |

FOREIGN PATENT DOCUMENTS

| | | |
|---|---|---|
| WO | WO81/00516 | 3/1981 |
| WO | WO92/22312 | 12/1992 |
| WO | WO94/20133 | 9/1994 |
| WO | WO96/17633 | 6/1996 |
| WO | WO97/42986 | 11/1997 |
| WO | WO01/97872 | 12/2001 |

OTHER PUBLICATIONS

J. Rousou et al., "Randomized Clinical Trial of Fibrin Sealant in Cardiac Surgery Patients Undergoing Resternotomy" Feb. 1989; Journal of Thoracic and Cardiovascular Surgery; vol. 97, No. 2, pp. 194-203.

P. Knoringer, "Fibrin Sealing in Spinal Neurosurgery" 1986.

P.M. McCarthy et al., "Fibrin Sealant: The Cleveland Clinic Experience" 1991.

M. Dahan et al., "The Importance of Biological Glue for the Prevention of Air Leakage in Pulmonary Surgery" 1991; Materials and Methods, pp. 113-116.

H. W. Waclawiczek, "Fibrin Sealing in Liver and Spleen Surgery" 1994.

C. Shaffey et al., "Neurosurgical Applications of Fibrin Glue: Augmentation of Dural Closure in 134 Patients" 1990; Neurosurgery, vol. 26, No. 2, pp. 207-210.

M. Acqui et al., "Our Experience With Human Fibrin Glue in Neurological Procedures" Date unknown.

A. Hjortrup, M.D. et al., "Fibrin Adhesive in Perineal Fistulas" Sep. 1991; from the Dept. of Surgical Gastroenterology F, Bispebjerg Hospital and Dept. of Surgical Gastroenterology C, Rigsbospitalet, University of Copenhagen, Copenhagen, Denmark, vol. 34, No. 9.

T. M. Kieser et al., "Reduced Postoperative Bleeding Following Use of Tisseel Fibrin Sealant in 300 Patients undergoing Open-Heart Surgery" date unknown.

W. D. Sponitz, M.D. et al., "Clinical Uses of Fibrin Sealant" 1999; Transfusion Therapy: Clinical Principles and Practice, Bethesda, MD: AABB Press.

N. Tajima et al., "Bone Grafts Using Fibrin Glue for Posterolateral Spinal Fusion and Total Hip Replacement with Central Migration" date unknown.

G. E. Lutz et al., "Flouroscopic Transforaminal Lumbar Epidural Steroids: An Outcome Study" Nov. 1998; Arch Phys Med Rehabil, vol. 79, pp. 1362-1366.

P. Goupille et al., "The Role of Inflammation in Disk Herniation-Associated Radiculopathy" Aug. 28, 1998; Semin Arthritis Rheum, (1):60-71.

J. D. Kang et al., "Herniated Lumbar Intervertebral Discs Spontaneously Produce Matrix Metalloproteinases, Nitric Oxide, Interleukin-6, and Prostaglandin E2" Feb. 1, 1996; Spine, 21(3): 271-7.

J. S. Saal et al., "High Levels of Inflammatory Phospholipase A2 Activity in Lumbar Disc Herniations" Jul. 1990; Spine, 15(7): 674-8.

O. P. Nygaard et al., "The Inflammatory Properties of Contained and Noncontained Lumbar Disc Herniation" Nov. 1, 1997; Spine, 22(21): 2484-8.

H. Takahashi et al., "Inflammatory Cytokines in the Herniated Disc of the Lumbar Spine" Jan. 15, 1996; Spine, 21(2):218-24.

Product Information, "Celestone Soluspan", brand of betamethasone sodium phosphate and betamethasone acetate Injectable Suspension, USP 6 mg. per mL, Schering Corporation, Kenilworth, N.J. 07033 USA, Rev. 3/96.

Product Information, "Fibrin Sealant Hemaseel APR Kit, Two Component Fibrin Sealant, Vapor Heated, Kit" Manufactured for and Distributed by Haemacure Corp., 2 N. Tamiami Trail, Suite 802, Sarasota, FL 34236, Issued May 1998.

PCT International Search Report, PCT/US05/39276, Jun. 6, 2006.

J.H. Boss et al., *"Osteonecrosis fo the Femoral Head of Laboratory Animals: The Lessons Learned from a Comparative Study of Osteonecrosis in Man and Experimental Animals."* Vet Pathol 40 (2003): 345-55.

Darrel E. Fisher, *"The Role of Fat Embolism in the Etiology of Corticosteroid-Induced Avascular Necrecosis: Clinical and Experimental Results."* Clinical Orthopaedics and Related Research (1978): 68-80.

* cited by examiner

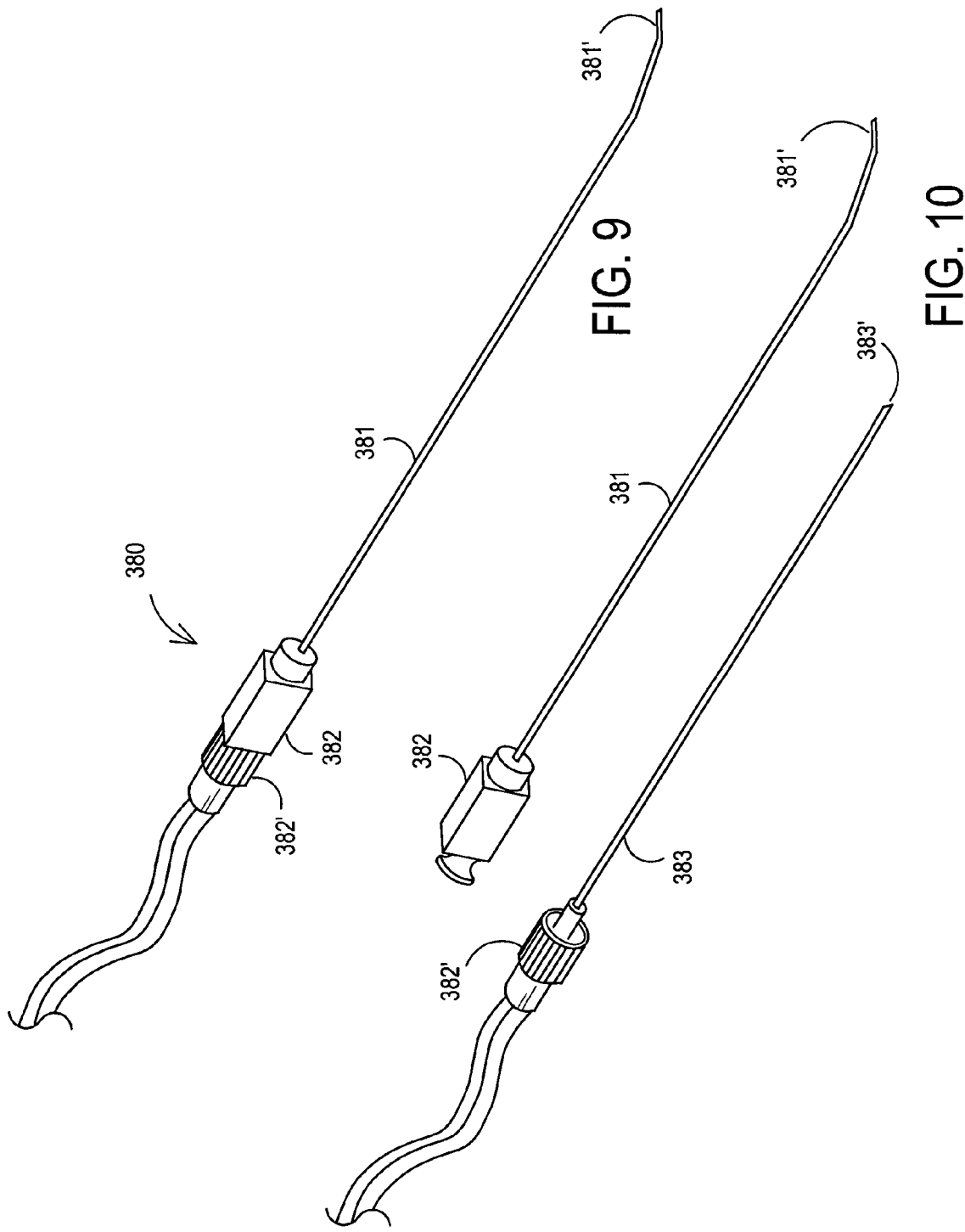

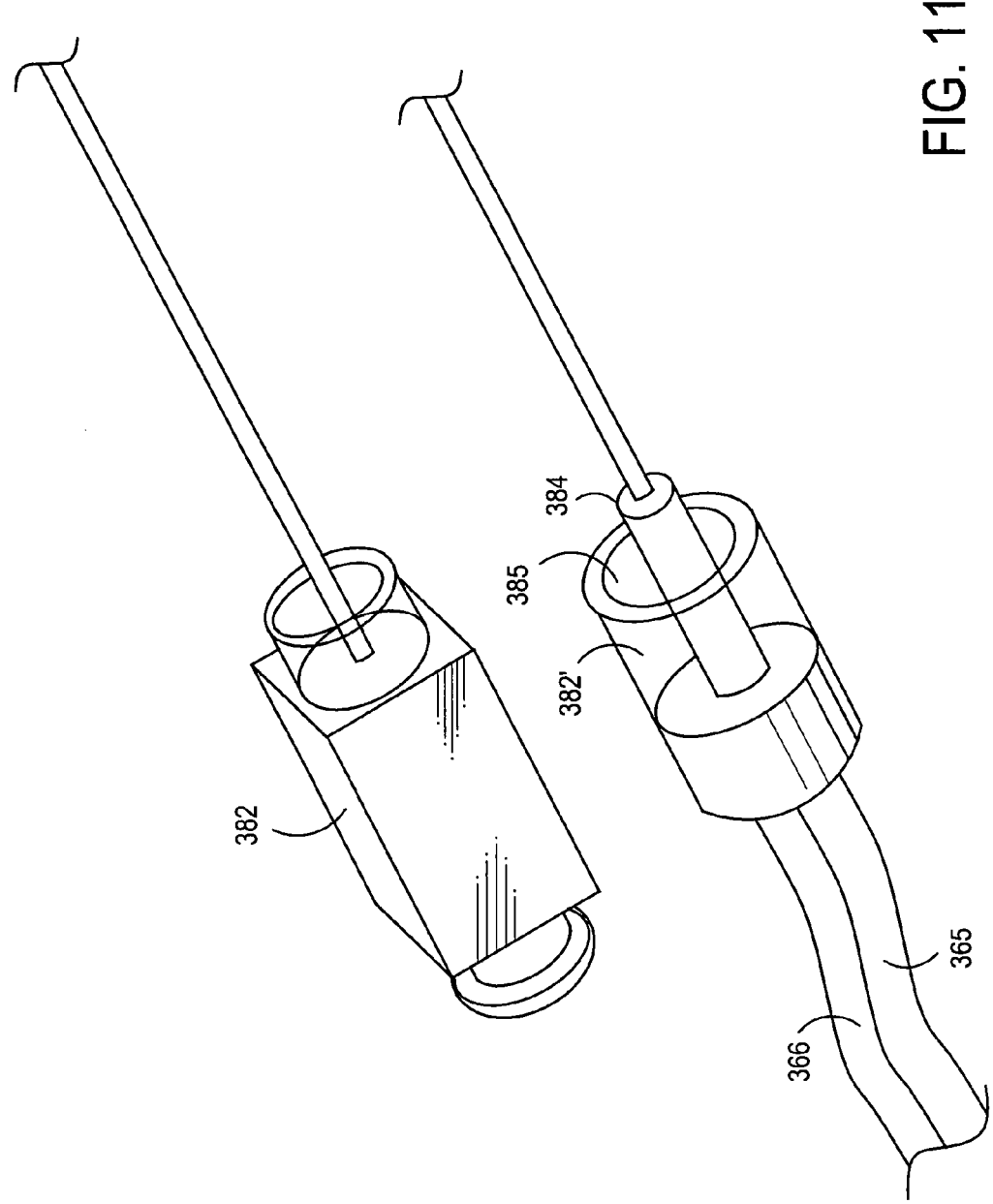

APPARATUS AND METHOD FOR INJECTION OF FIBRIN SEALANT IN SPINAL APPLICATIONS

This application claims priority to U.S. provisional application No. 60/623,600, filed Oct. 29, 2004 and is a continuation-in-part of U.S. application Ser. No. 11/205,760, filed Aug. 17, 2005, of U.S. application Ser. No. 11/205,784, filed Aug. 17, 2005, and of U.S. application Ser. No. 11/205,775, filed Aug. 17, 2005, now U.S. Pat. No. 7,597,687, and to U.S. provisional application No. 60/764,020, filed Feb. 1, 2006, and to U.S. provisional application No. 60/854,413, filed Oct. 24, 2006, all of which are incorporated herein by reference.

BACKGROUND OF THE INVENTION

The present invention relates generally to the use of fibrin sealant whereby the sealant is delivered such as by injection to the spinal area, and more particularly through use of a multi-lumen catheter.

Fibrin sealants, and glues, are well known and are used extensively in various clinical settings. Such sealants are indicated as adjuncts to hemostasis in surgeries when control of bleeding by conventional surgical techniques, including suture, ligature, and cautery is ineffective or impractical. In these cases, the sealant was applied topically.

Recently, fibrin sealant that included a corticosteroid was used to treat spinal disc joint problems such as fissures in the annulus fibrosus. In this regard, U.S. Pat. No. 6,468,527 discloses that the composition was injected into a disc (an intradiscal injection) to treat disc problems. In U.S. Pat. No. 6,468,527 the fibrin sealant is injected by inserting an introducer needle into disc, inserting a second needle through the introducer needle that is connected to a dual barrel syringe, and then injecting the fibrinogen and thrombin into the disc. The fibrinogen and thrombin begin mixing at the "Y" connection and throughout the length of the needle.

However, the inventors have recognized that a problem exists in that existing commercially available fibrin sealant forms fibrin so quickly that the needle can become completely clogged and blocked during injection, particularly if the fibrinogen and thrombin are being slowly injected. In addition, the needle becoming block can occur if two or more discs are being treated such that the second needle is removed and inserted into a second introducer needle. In both cases, the blockage of the needle can result in inadequate fibrin sealant, or no fibrin sealant, being introduced into the disc. The inventors have determined that a solution to this problem would be highly desirable.

SUMMARY OF THE INVENTION

This invention provides a solution to the problems and disadvantages discussed above.

In the practice of the present invention, a biologic sealant such as fibrin sealant can be introduced into, for example, the spinal area of a human being. Fibrin sealant comprises fibrinogen and thrombin, which form fibrin when mixed. Calcium chloride may be included in the fibrin sealant. The fibrin may optionally include one or more additives, such as various biological and non-biological agents.

In one broad respect, this invention is an apparatus for delivery of a sealant to, for example, the spinal area wherein the apparatus comprises at least two fluid reservoirs, an introducer needle having a distal tip that is in fluid communication with at least one reservoir, a fluid delivery tube that is in fluid communication with a second reservoir, wherein the fluid delivery tube has a tip and wherein the fluid delivery tube is configured so that the tip of the fluid delivery tube does not extend past the distal tip of the introducer needle during use. The device can be of virtually any configuration which permits delivery of the biologic sealant and which includes a fluid delivery tube that does not extend past the tip of the introducer needle. The at least two reservoirs may be in the form of a multi-barrel syringe or a multi-cylinder cartridge. In one embodiment, a connector couples to a second barrel of the multi-barrel syringe or to a second cylinder of the cartridge, wherein the connector is coupled to the introducer needle and the connector is adapted to receive the fluid delivery tube so that the fluid delivery tube extends into the introducer needle. The device can be manually actuated by application of pressure to a trigger such that the force exerted by the surgeon causes sealant to be injected, for example, or alternatively can be controlled by a computer (onboard or external) or the like so that sealant is automatically injected. If the sealant is automatically injected, the device may include servos, pneumatic actuators, or the like to facilitate injection. In one embodiment, the device comprises at least two reservoirs for fluids to be delivered, an actuation assembly that causes the fluids to flow out of the reservoir through an exit port in the reservoir, a housing that contains the reservoirs, a trigger that drives the actuation assembly, and an inner and outer needle wherein the fluid delivery tube does not extend past the distal tip of the outer (introducer) needle. The device may optionally include a pressure monitor. Typically, the device is held by the surgeon during use. Thus, the device can be hand-held as that term is understood in the art. Alternatively, the device can be adapted to be held by a stationary arm, robotic arm, or the like prior to, during, or after injection of the sealant.

The reservoirs can take the form of bores in a cartridge, the bores of two syringes, or the like. The bores may have plungers therein, which serve to drive the fluids out of the bores. In these embodiments, the actuation assembly serves to engage the plungers so that the plungers drive the fluids out of the bores. The actuation assembly is actuated by pressure applied to a trigger.

In one respect, the device comprises a cartridge having at least two cylinder bores for fluids to be delivered, wherein each cylinder includes an exit port for a fluid, a plunger within each cylinder for pushing the fluids out of the cylinder, a housing adapted to receive the cartridge, wherein the housing includes an adaptor to receive and lock a manifold that operably connects to the exit ports of the cartridge, at least two toothed rams, wherein each toothed ram is at least partially within a cylinder bore, a trigger connected to the housing, wherein the trigger includes a toothed drive rack, a toothed wheel assembly that cooperates with the toothed drive rack and with the toothed rams, and wherein an inner and outer needle wherein the inner needle does not extend past the distal tip of the outer (introducer) needle. The inner needle is in fluid communication (coupled) to one of the reservoirs and the outer needle is in fluid communication with the other reservoir, typically coupled through an appropriately designed luer fitting as would be readily apparent to one of skill in the art. In one embodiment, the actuation assembly comprises the rams, the drive rack, and the wheel assembly. In certain embodiments if a pressure monitor is present, the pressure monitor is contained within the housing; the pressure monitor includes a display that is positioned toward the rear of the device above the handle; the pressure monitor includes a display that is flush with the housing; the pressure monitor is an electronic pressure monitor; the pressure monitor includes a pressure transducer that is operably attached to at least one reservoir; the pressure monitor alerts the surgeon if fluid pressure reaches a given level; the pressure monitor alerts the surgeon if fluid pressure reaches a given level by emitting a sound; the pressure monitor alerts the surgeon if fluid pressure reaches a given level by flashing a signal; the pressure monitor alerts the surgeon if fluid pressure reaches a given level by causing the apparatus to vibrate; the pressure monitor is adapted to be set by the surgeon to a given maximum pressure; the pressure monitor stops further pressure increase of the fluid if fluid pressure reaches a given level; the pressure monitor provides data to a computer; and combinations thereof.

In alternative embodiments, the pressure monitor is contained within the housing; the pressure monitor includes a display that is positioned toward the rear of the device above the handle; the pressure monitor includes a display that is flush with the housing; the pressure monitor may be a pneumatic, electric, hydraulic or a hybrid pressure monitor. The pressure monitor can provide a visual alert to the surgeon if fluid pressure reaches a given level; the pressure monitor alerts the surgeon if fluid pressure at the manifold reaches a given level by means of a calibrated needle or similar indicator on a marked dial or graduated cylinder. Calibrated graduations may be numerically defined or indicated by some defined color scheme.

In another broad respect, this invention is an apparatus for injecting fibrin sealant into a human disc, comprising: a multi-barrel syringe, an introducer needle having a distal tip, a fluid delivery tube that directly or indirectly couples to a first barrel of the multi-barrel syringe, wherein the fluid delivery tube has a tip and wherein the fluid delivery tube is configured so that the tip of the fluid delivery tube does not extend past the distal tip of the introducer needle during use; and a connector coupled to a second barrel of the multi-barrel syringe, wherein the connector is coupled to the introducer needle and the connector is adapted to receive the fluid delivery tube so that the fluid delivery tube extends into the introducer needle.

In another broad respect, this invention is a method of treating a disc that is leaking nucleus pulposus into and or through at least one defect in the annulus fibrosus, comprising: inserting an introducer needle that can be attached to a connector into the disc, wherein the introducer needle has a distal tip; inserting a fluid delivery tube that is attached to the connector into the introducer needle, wherein the fluid delivery tube has a tip and wherein the fluid delivery tube is configured so that the tip of the catheter does not extend past the distal tip of the introducer needle; injecting a biologic sealant, such as fibrinogen solution and activating solution, so that components of the biologic sealant (such as a fibrinogen solution and an activating solution) begin mixing after the connector and within the space between the distal tip of the introducer needle and the tip of the fluid delivery tube.

In another broad respect, this invention is a method of treating a disc, comprising injecting biologic sealant into the disc using a delivery apparatus, wherein the apparatus comprises at least two fluid reservoirs, an introducer needle having a distal tip that is in fluid communication with at least one reservoir, a fluid delivery tube that is in fluid communication with a second reservoir, wherein the fluid delivery tube has a tip and wherein the fluid delivery tube is configured so that the tip of the fluid delivery tube does not extend past the distal tip of the introducer needle during use.

In another broad respect, this invention is a method of treating joints in the spinal area. Other than spinal disc joints, this may include other articulating joints of the spine such as the sacroiliac joint, the lateral atlanto-axial joint or the thoracic zygapophysial joint. This invention is a method of treating joints comprising injecting a biologic sealant such as fibrin sealant into a joint to seal at least one defect of a joint capsule, and wherein the biologic sealant is injected while using a delivery apparatus that includes a pressure monitor to measure the pressure of the fibrin sealant being injected. If the biologic sealant is fibrin sealant, the fibrin sealant may comprise fibrinogen and an activating compound such as thrombin, wherein the fibrinogen and activating compound forms at least a portion of the fibrin after injection into the joint. In one embodiment, the fibrinogen is autologous.

This invention, in another broad respect, is a kit, comprising: a biologic sealant, and a biologic sealant apparatus for injecting fibrin sealant into a human disc, wherein the apparatus is equipped with a fluid delivery tube and an introducer needle, wherein fluid delivery tube has a tip and wherein the fluid delivery tube is configured so that the tip of the fluid delivery tube does not extend past the distal tip of the introducer needle. In the case of fibrin sealant, the components may comprise fibrinogen, such as freeze-dried fibrinogen, thrombin such as freeze-dried thrombin, and the delivery device. The kit can optionally include contrast agent and other additives. This invention, in one embodiment, is a kit, comprising: fibrinogen, an activating compound, and a fibrin sealant delivery apparatus for injecting fibrin sealant into a human disc, wherein the apparatus is equipped with a fluid delivery tube and an introducer needle, wherein the fluid delivery tube has a tip and wherein the fluid delivery tube is configured so that the tip of the fluid delivery tube does not extend past the distal tip of the introducer needle.

In another broad respect, this invention is a process for forming a kit, comprising: providing a biologic sealant, and a biologic sealant apparatus for injecting fibrin sealant into a human disc, wherein the apparatus is equipped with a fluid delivery tube and an introducer needle, wherein the fluid delivery tube has a tip and wherein the fluid delivery tube is configured so that the tip of the fluid delivery tube does not extend past the distal tip of the introducer needle. This invention, in one embodiment, is a kit comprising a fibrinogen component, an activating compound, and a fibrin sealant delivery apparatus for injecting fibrin sealant into a human disc, wherein the apparatus is equipped with a polymeric multilumen catheter.

In another broad respect, this invention is a method of manufacturing an apparatus for injecting fibrin sealant into a human disc, comprising: providing at least two reservoirs such as a multi-barrel syringe or multi-cylinder cartridge, providing an introducer needle having a distal tip, providing a fluid delivery tube that directly or indirectly couples to one reservoir, wherein the fluid delivery tube has a tip and wherein the fluid delivery tube is configured so that the tip of the fluid delivery tube does not extend past the distal tip of the introducer needle during use. In one embodiment, the method includes providing a connector coupled to a second reservoir, wherein the connector is coupled to the introducer needle and the connector is adapted to receive the fluid delivery tube so that the fluid delivery tube extends into the introducer needle.

The defect to be treated in accordance with this invention includes but is not limited to a tear of the annulus fibrosus, a fissure in the annulus fibrosus, the fibrous capsule of a spinal joint and the like. This treatment serves to reduce the amount of material from the nucleus pulposus that leaks through the defect(s) in the annulus fibrosus, and or the potential in-growth of granular tissue and coincidental innervation which may be a source of pain not normally present in a healthy joint. Alternately, this treatment may insulate innervated granular tissue from the effects of nucleus pulposus. The presence of this innervated granular tissue sometimes found within the annulus at the site of an anular defect or tear, is believed to be a common physiologic healing response. Advantageously, injection of the fibrin sealant can also serve to restore normal disc (or joint) height and physiologic hydrostatic pressure, key components to disc health. It should be understood that normal physiologic hydrostatic pressure can vary from person to person, and that the treatment may produce near-normal hydrostatic pressure. As used herein, normal physiologic pressure encompasses this range of pressures. In one embodiment, neither the nucleus pulposus nor the annulus fibrosus has been heated in the body to stiffen the disc either prior to or concurrent with the injection, such as discussed in for example U.S. Pat. No. 6,095,149. In one embodiment, in the practice of this invention the nucleus pulposus has not been removed by surgery, such as in the case of a total or partial discectomy or by nucleoplasty for a herniated disc.

Advantageously, the method and kit of this invention facilitate extended pain relief for patients with discogenic pain, wherein for example nucleus pulposus leaks out of the disc through defects (e.g. tears or fissures) in the annulus fibrosus.

Additionally, the method and kit of this invention facilitate extended pain relief for patients with other spinal joint pain, wherein for example of the potential in-growth of granular tissue and coincidental innervation which may be a source of pain not normally present in a healthy joint. Alternately, this treatment may insulate innervated granular tissue from the effects of nucleus pulposus.

BRIEF DESCRIPTION OF THE DRAWINGS

FIGS. 9-11 show one embodiment of the needle assembly of this invention.

DETAILED DESCRIPTION OF THE INVENTION

In general, the delivery device includes at least two reservoirs, an introducer needle, a fluid delivery tube adapted to receive fluid from a first reservoir and adapted to extend into the introducer needle such that the tip of the tube does not extend beyond the tip of the introducer needle, and a connector coupled to a second reservoir, wherein the connector is coupled to the introducer needle and adapted to receive the fluid delivery tube so that the fluid delivery tube extends into the introducer needle. The apparatus can optionally include a pressure monitor. If present, the pressure monitor couples to the delivery device through a line connected to a transducer in, for example, one of the reservoirs. Alternatively, the transducer can be located within the connector, or anywhere else where the transducer can be introduced within the device such that pressure of within the device can be measured.

In certain embodiments, the fluid delivery tube can be a needle or a catheter. In one embodiment, the fluid delivery tube attaches directly to a syringe, such as by way of a luer fitting. Alternatively, the fluid delivery tube may be integral with the connector. For example, the connector can be made by forming the connector around a portion of the needle in an injection molding process or other process.

Pressure monitors are available commercially. For example, a suitable pressure monitor is currently available from Merit Medical Systems, Inc. (Utah, US) sold as a Meritrans™ transducer. Other representative pressure monitors are disclosed in, for example, U.S. patent application Ser. No. 2005/0004518, incorporated herein by reference. In the device disclosed in 2005/0004518, a pressure transducer is integrally mounted in the plunger of a syringe under the plunger tip such that the force applied by the plunger to the fluid in the syringe is transmitted to the transducer and the resulting electronic signal is converted to a display value, aiding the physician in diagnosing diseased disks in the back. The transducer of the pressure monitor can be positioned in the barrel of a syringe or, alternatively, in the connector (or "hub").

Figure 1A:
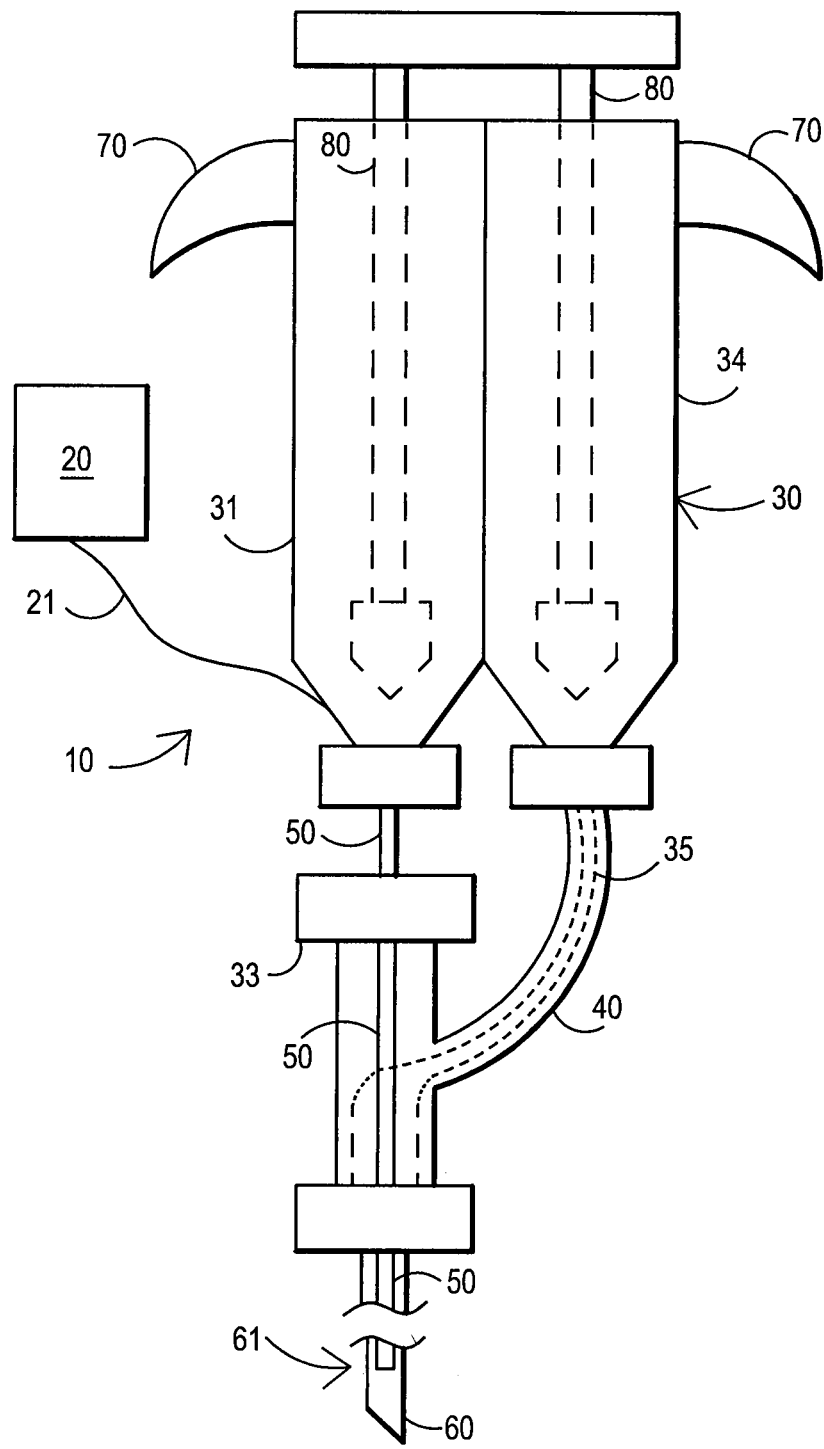
FIGS. 1A, 1B and 1C show representative delivery devices of this invention.
Figure 1B:
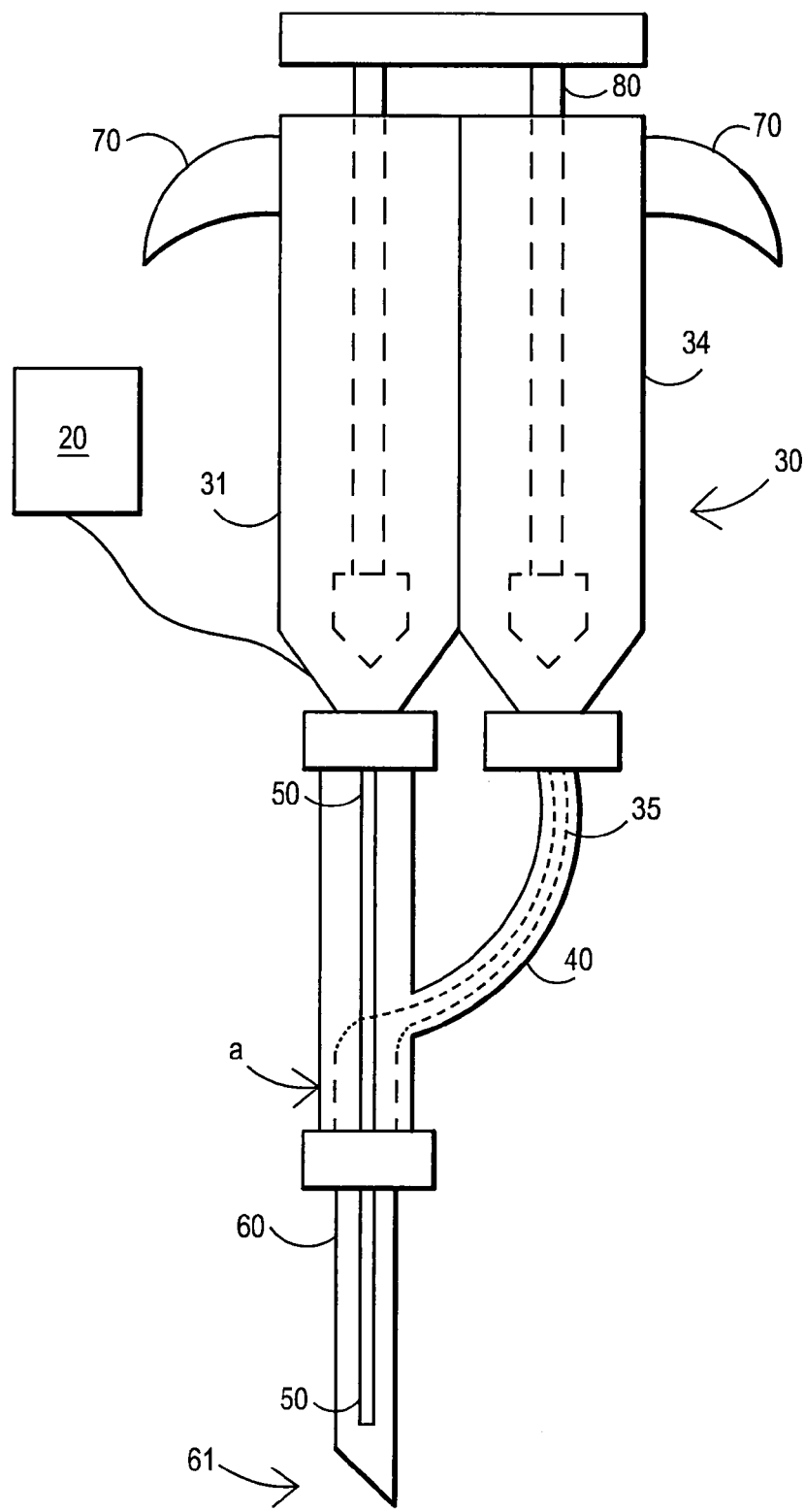
Figure 1C:
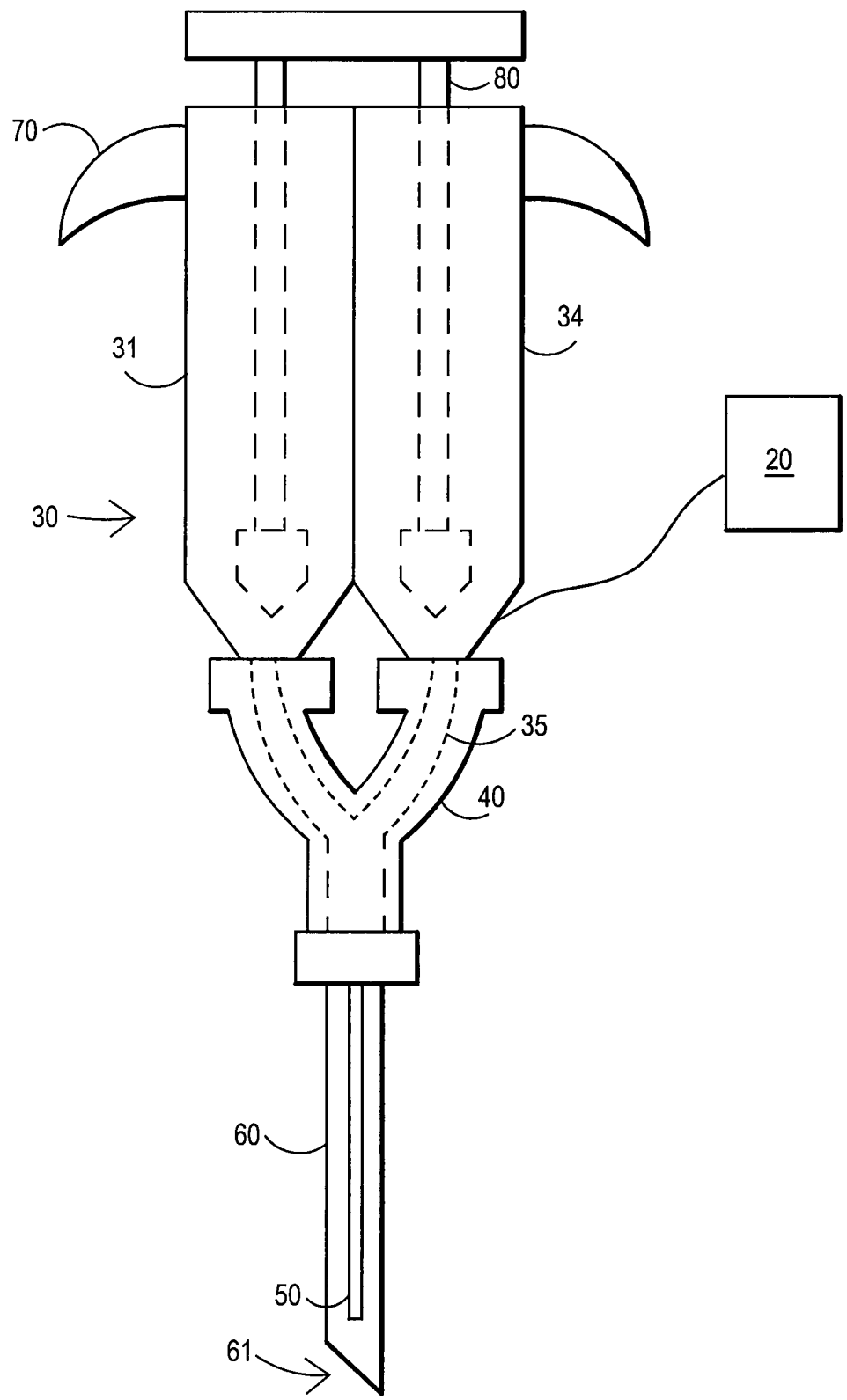

FIGS. 1A, 1B, and 1C illustrate representative devices of this invention that have been fully assembled. Each device is adapted for use to deliver fibrin sealant. In FIG. 1, the device 10 includes a pressure monitor 20, fluid reservoirs (such as a multi-barrel syringe) 30, a connector 40, a fluid delivery tube 50, and an introducer needle 60. The syringe, connector, and needle can be coupled using standard luer fittings. The fluid reservoirs can include handles 70 and plungers 80. Alternatively, the fluid reservoirs can be configured such that the reservoirs are flexible and can be squeezed or rolled to force fluids out. The introducer needle 60 can, for example, couple to the connector by a luer fitting at an end of the connector opposite to the end connected to the syringe. In FIG. 1, the fluid from barrel 31 is driven through a fluid delivery tube 50 that has been pushed through a plug 33 attached to or integral with the connector 40, with the fluid delivery tube being of sufficient length to be threaded into the introducer needle. Thus, in one embodiment, the fluid delivery tube 50 couples to a first barrel 31 of a multi-barrel syringe and the fluid delivery tube extends into the connector through a plug coupled to the connector. In one embodiment, the fluid delivery tube directly couples to the first barrel of the syringe, and the fluid delivery tube is affixed to the connector so that the fluid delivery tube cannot move within the introducer needle. Fluid from barrel 34 is pushed through a conduit 35 within the connector and flows into the introducer needle. Thus, the connector is adapted for conveying fluid from the fluid delivery tube into the introducer needle. The connector can include a passage 35 for fluid from the second barrel to the introducer needle, with the passage being of a diameter such that the fluid from the second syringe barrel is of a volume approximately equal to the volume of fluid delivered through the fluid delivery tube. In one embodiment, the fluid delivery tube is of a length such that it does not protrude out the end of the introducer needle. The fluids from barrel 31 and 34 mix near the distal tip 61 of the introducer needle 60. The pressure monitor 20 couples to barrel 31 via line 21 that is attached to a transducer such that the transducer of the pressure monitor is within the barrel to measure internal pressure within the barrel. The pressure measured within the barrel will be the same or nearly the same pressure as that at the distal tip of the introducer needle during a procedure. Thus, the pressure monitor allows the pressure within the disc to be monitored. In one embodiment, the multi-barrel syringe 30 has two barrels. Each barrel can be configured to couple to the connector or fluid delivery tube by a luer fitting. A delivery device of this invention may be equipped with a trip switch if a given pressure is reached, which reduces the chance of an overpressurized disc.

The device depicted in FIG. 1B is similar to the device in FIG. 1A except that in FIG. 1B the fluid delivery tube 50 is integral with the connector so that the fluid delivery tube does not need to be inserted through a plug. The fluid delivery tube can be bonded to the connector or can be otherwise coupled to the connector so that fluid from the barrel flows into the fluid delivery tube. It should be appreciated that a first fluid, such as fibrinogen, is injected through either the fluid delivery tube 50 or through the conduit 35, with the activating compound being injected through the opposite passage from that used by the fibrinogen. Thus the two fluids flow through the device in coaxially and do not touch or mix until the given fluid exits the fluid delivery tube 50. Line "a" points to an alternative location for the transducer of the pressure monitor.

FIG. 1C depicts device 10 that includes a pressure monitor 20, a reservoir which in this case is a multi-barrel syringe 30, a Y-connector 40, a fluid delivery tube 50, and an introducer needle 60. In this embodiment, barrel 31 and barrel 34 are coupled to the Y-connector 40 such as through luer fittings. Fluid from barrels 31 and 34 flow into the Y-connector where mixing begins. The fluids then enter the fluid delivery tube 50, which extends into the introducer needle 60. The introducer needle 60 couples to the connector 40 via a luer fitting. In this embodiment, the pressure monitor is coupled to barrel 34 (the transducer is within barrel 34).

It should be appreciated that a wide variety of designs can be used for the fluid delivery device. For example, the device can include a delivery gun equipped with a ratcheting lever to make injection easier. Such a delivery gun could also be automated so that physical pressure is not needed by the physician in order for injection to proceed. It is envisioned that if such a delivery gun was used, the gun could be loaded with the multiple barrels that contain the fibrinogen and activating compound liquids. Compression of the lever would force plungers to push the fluids from out of the barrels and into the connector, fluid delivery tube, and/or introducer needle. Alternatively, the gun could use a screw-type action to move the plungers. Either embodiment gives the physician a mechanical advantage when injecting the components. What is important, however, is that in this invention the pressure monitor is always coupled to the delivery device.

Figure 2:
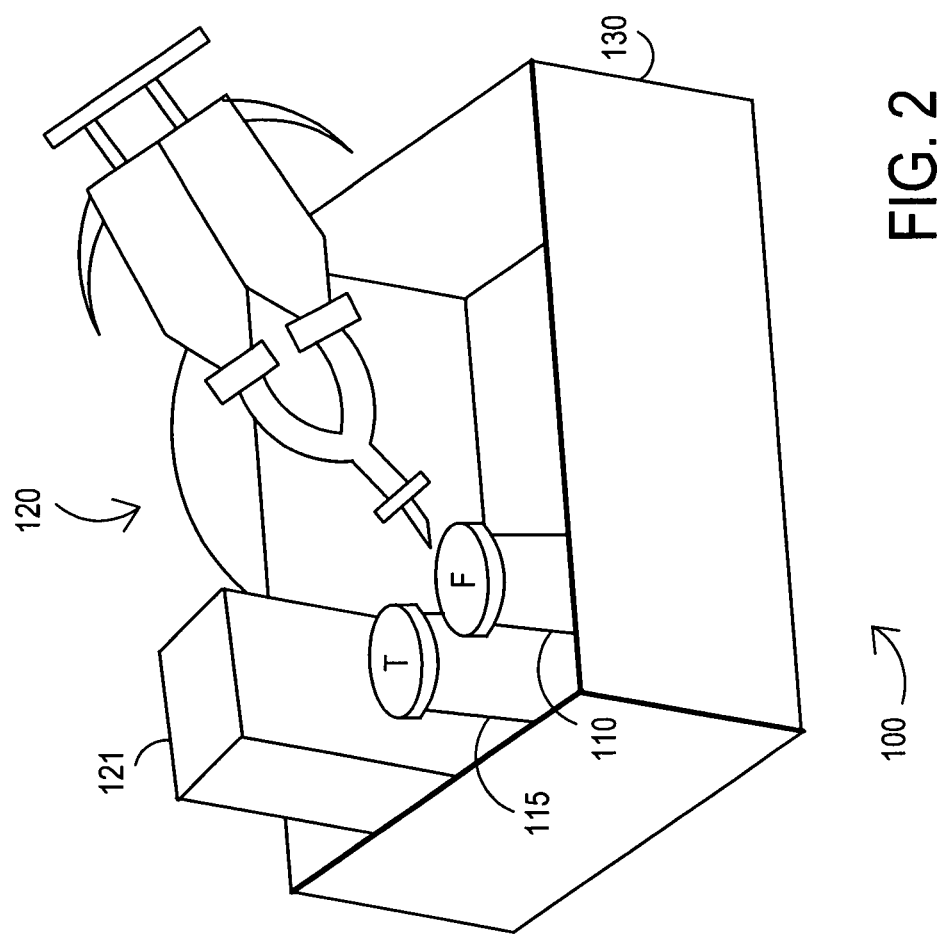
FIG. 2 shows another representative apparatus of this invention that includes an integrated coaxial flow connector ("hub").

FIG. 2 shows a representative kit of this invention. The kit 100 includes fibrinogen 110, an activating compound 115, and a fibrin sealant delivery apparatus 120 for injecting fibrin sealant into a human disc, wherein the apparatus is equipped with a pressure monitor 121. The kit may be stored and shipped in a suitable container 130. The kit may include additional items, such as but not limited to one or more additives, a source of calcium ions, a device for reconstituting freeze-dried fibrinogen, additional fluid delivery tubes, additional introducer needles, and so on.

Figure 3B:
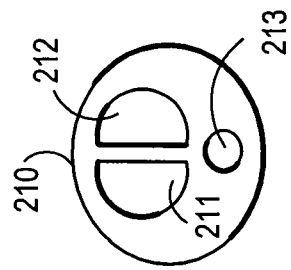
FIGS. 3A, 3B, and 3C show representative cross-sectional views of multi-lumen catheters.
Figure 3C:
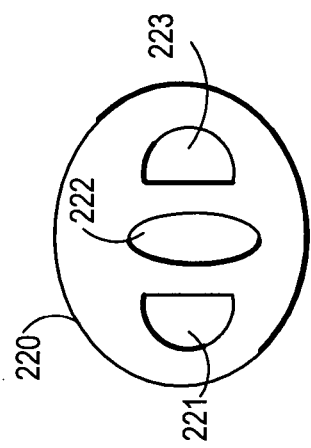
Figure 3A:
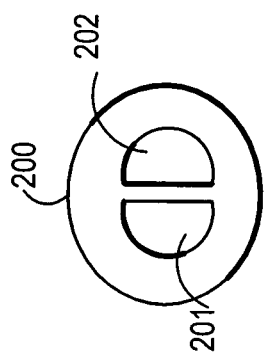

FIGS. 3A and 3B show representative cross-sectional views of multi-lumen catheters. FIG. 3A shows a bitumen catheter 200 wherein the lumen are in side-by-side arrangement and in which fibrinogen would be injected through lumen 201 and the activating compound through lumen 202. In FIG. 3B a trilumen catheter 210 is depicted wherein a first lumen 211 may carry one fluid, second lumen 212 carries a second fluid, and a third lumen 213 may carry an additive or have a wire inserted through the lumen 213 to improve the physical integrity and rigidity of a polymeric catheter. FIG. 3C depicts a trilumen catheter 220 wherein the lumen 221, 222, and 223 are arranged in sequence (in side-by-side relationship). A multi-lumen catheter can be used in this invention. A multi-lumen catheter can have a number of cross-sectional structures. The catheter can also have more than three lumen.

Figure 4:
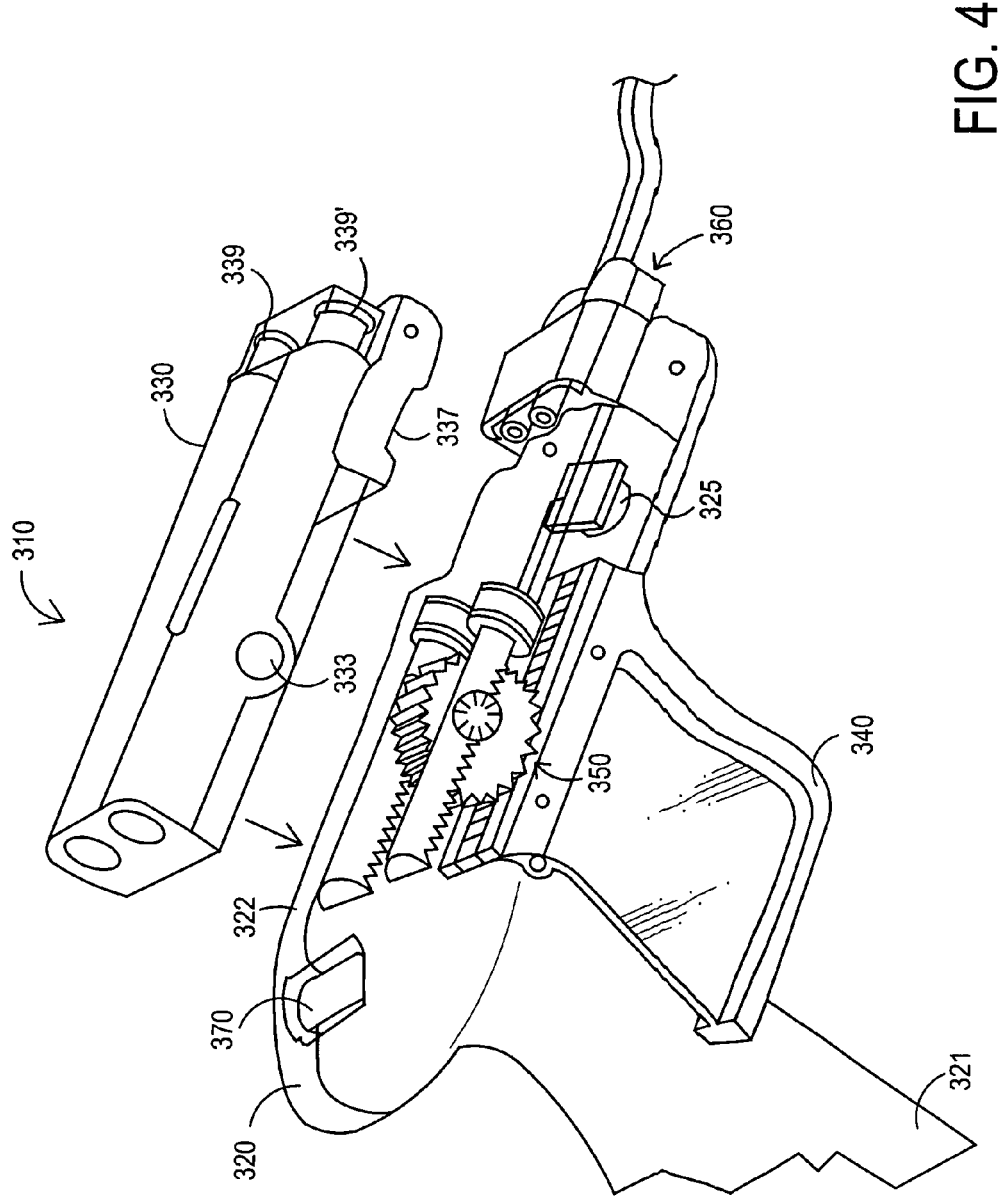
FIG. 4 shows a semi-exploded view of one embodiment of the device of this invention.

Referring now to FIG. 4, a representative delivery device of this invention is depicted. The device 310 includes a housing 320 that holds or is connected to some of the device's parts. The housing can be made from a variety of materials, but is typically made from one or more plastic materials. The housing can generally be referred to as being in the shape of a pistol, including a handle 321 and barrel 322. At least two reservoirs (cartridge) 330 is positioned within the barrel 322. The housing is adapted to receive and house the cartridge. The cartridge 330 is thus positioned within the barrel 322. The housing can be a multi-piece component, such as a two piece housing that is assembled using screws, or configured using snap-in type functionality. The specific design shown in FIG. 4 is merely representative and not intended to limit the types of housings employed in the practice of this invention.

In addition, a trigger 340 is operably connected to and situated within the housing so that the trigger 340 can slide from a first position into the housing to a second position as pressure is applied by the operator to the trigger 340. The housing 320 can include an internal stop, not shown, for the travel of the trigger 340.

Figure 5:
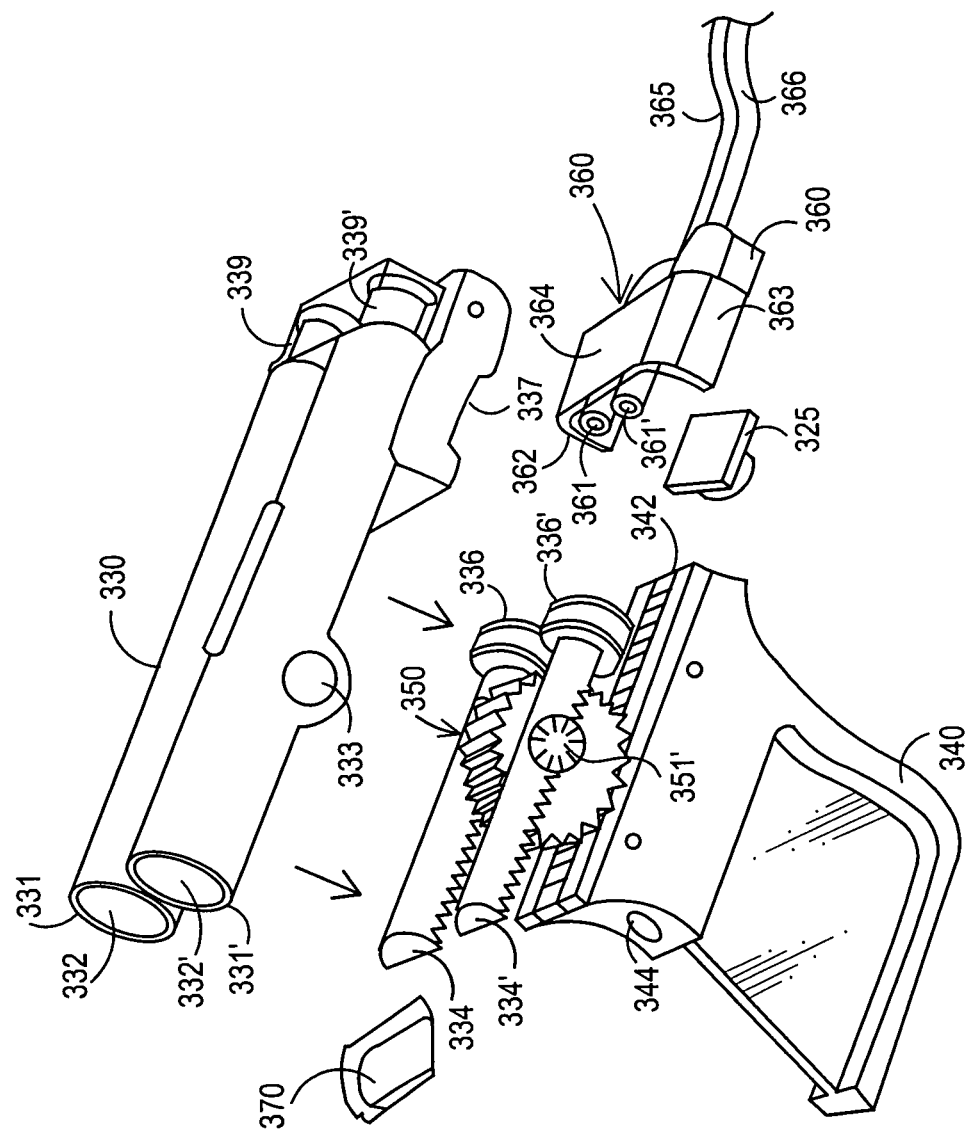
FIG. 5 shows a semi-exploded view of components of one embodiment of the device of this invention.
Figure 6:
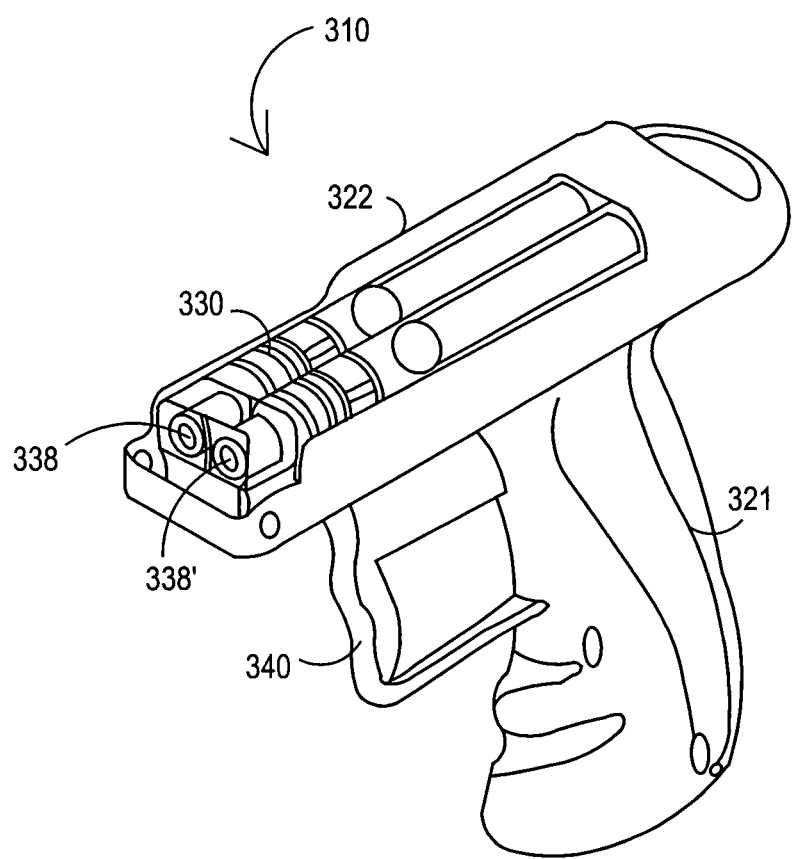
FIG. 6 shows a device of this invention, including exit ports 338, 338' of the cartridge 30.
Figure 7:
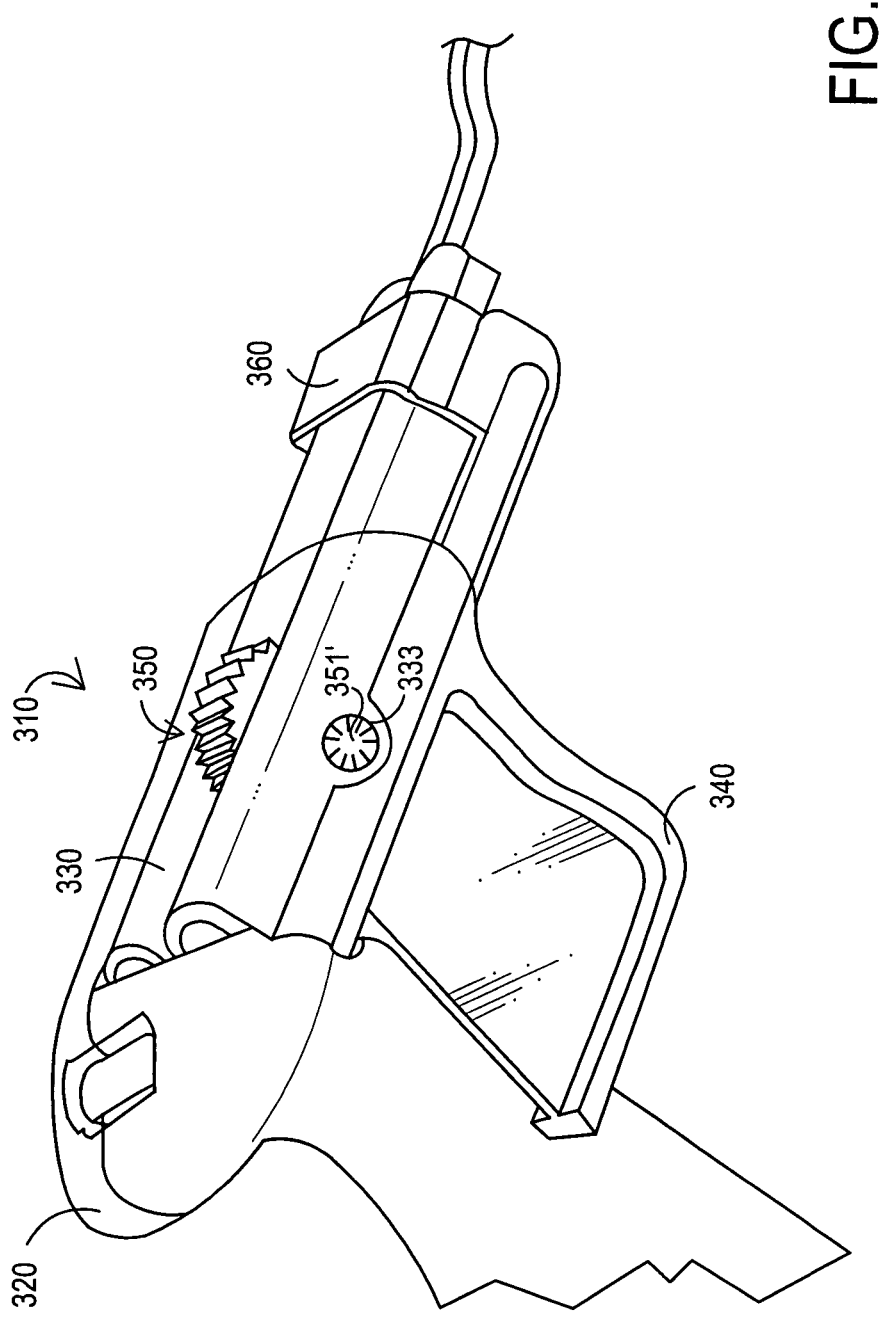
FIG. 7 shows a perspective view of the device of this invention.
Figure 8:
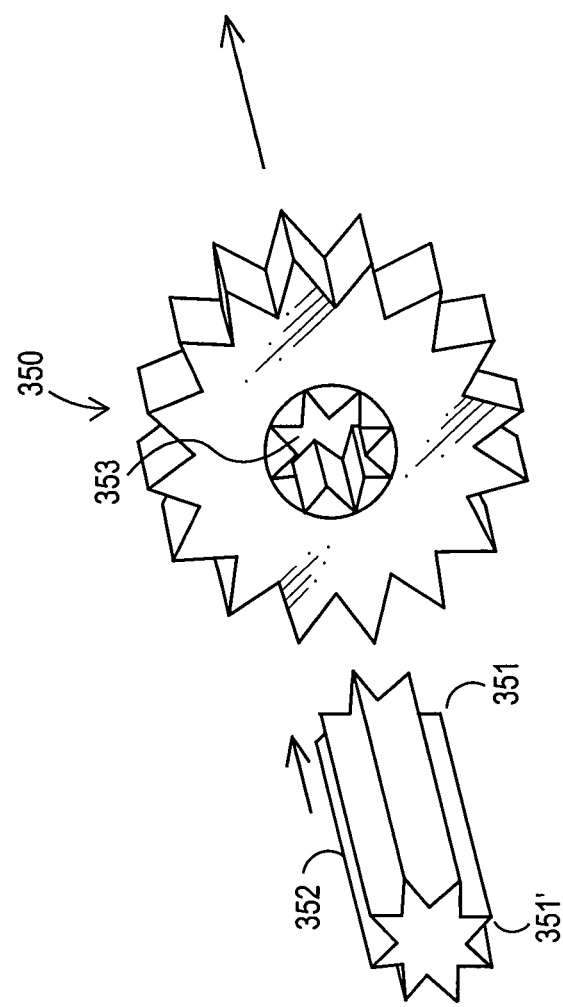
FIG. 8 shows a wheel assembly used in one embodiment of the device of this invention.

The cartridge 330 is depicted in greater detail in FIG. 5. Thus, the cartridge 330 includes two cylinders 331, 331' that each has a bore 332, 332' for receipt of a fluid. Each cylinder 331, 331' defines a generally straight tube having the same diameter for the length of the bores 332, 332'. The cartridge 330 may include one or more fittings, slots, or the like that serve to secure the cartridge 330 within the housing. For example in FIG. 5 the housing includes a fitting 353 that is configured to fit within slot 337 of the cartridge to thereby secure cartridge 330 from lateral movement. It should be appreciated that the cartridge 330 does not move upon application of pressure to the trigger 340. Rather, application of pressure to the trigger 340 engages the rack 342, wheel assembly 350, and rams 334, 334' to push the plungers 336, 336' toward the exit ports 338, 338' (see FIG. 6) of the cartridge 330. In FIG. 8, the extended gear ends 351, 351' of the wheel assembly 350 fit into bore 333 of the cartridge 330 (see also FIG. 7). It should be appreciated that the cartridge 330 can be integral with the housing 320. That is, the cartridge 330 need not be a separate and/or detachable component that is placed within the housing but instead can be formed as part of the housing during fabrication of the housing.

It should be appreciated that the wheel assembly 350 can be a single piece or can be assembled from multiple parts to form the assembly. Thus, for example, with respect to a multiple-part assembly, as depicted in FIG. 8, a toothed internal gear 352 having extended gear ends 351, 351' is inserted into internal bore 353 of wheel 350. The gear 352 is adapted to engage the wheel 350, such as by interdigitating teeth, so that the assembly would move as a single part during use of the device 310. In this embodiment, the inner toothed gear 352 can be seen to be sandwiched between the extended gear ends 351, 351'. Alternatively, the wheel assembly can be cast, forged, milled, or otherwise formed to manufacture a single monolithic wheel assembly. Alternatively to teeth, the wheel assembly 350, rack 342, and rams can be made of materials that engage with sufficient friction to provide the desired movement, using for example tacky rubber materials, materials have a grainy surface (e.g., with a sand-paper like finish), and so on.

Referring again to FIG. 5, there is shown a pressure readout display 370 that provides the surgeon with a pressure reading within one of the bores 332, 332' of the cartridge 330. A transducer, not shown, is configured to measure pressure within a bore and a line, not shown, from the transducer to the display 370 provides a signal to electronic circuitry that processes the signal and provides a reading to display 370. Thus, the pressure monitor couples to the delivery device through a line connected to a transducer in, for example, one of the syringes. Alternatively, the transducer can be located within the connector, or anywhere else where the transducer can be introduced within the device such that pressure of within the device can be measured. Preferably, the transducer is in the bore. The display can be but is not limited to an LCD.

Pressure monitors are available commercially. For example, a suitable pressure monitor is currently available from Merit Medical Systems, Inc. (Utah, US) sold as a Meritrans™ transducer. Other representative pressure monitors are disclosed in, for example, U.S. patent application Ser. No. 2005/0004518, incorporated herein by reference. In the device disclosed in Ser. No. 2005/0004518, a pressure transducer is integrally mounted in the plunger of a syringe under the plunger tip such that the force applied by the plunger to the fluid in the syringe is transmitted to the transducer and the resulting electronic signal is converted to a display value, aiding the physician in diagnosing diseased disks in the back. The transducer of the pressure monitor can be positioned in the barrel of a syringe or, alternatively, in the connector (or "hub").

Figure 12:
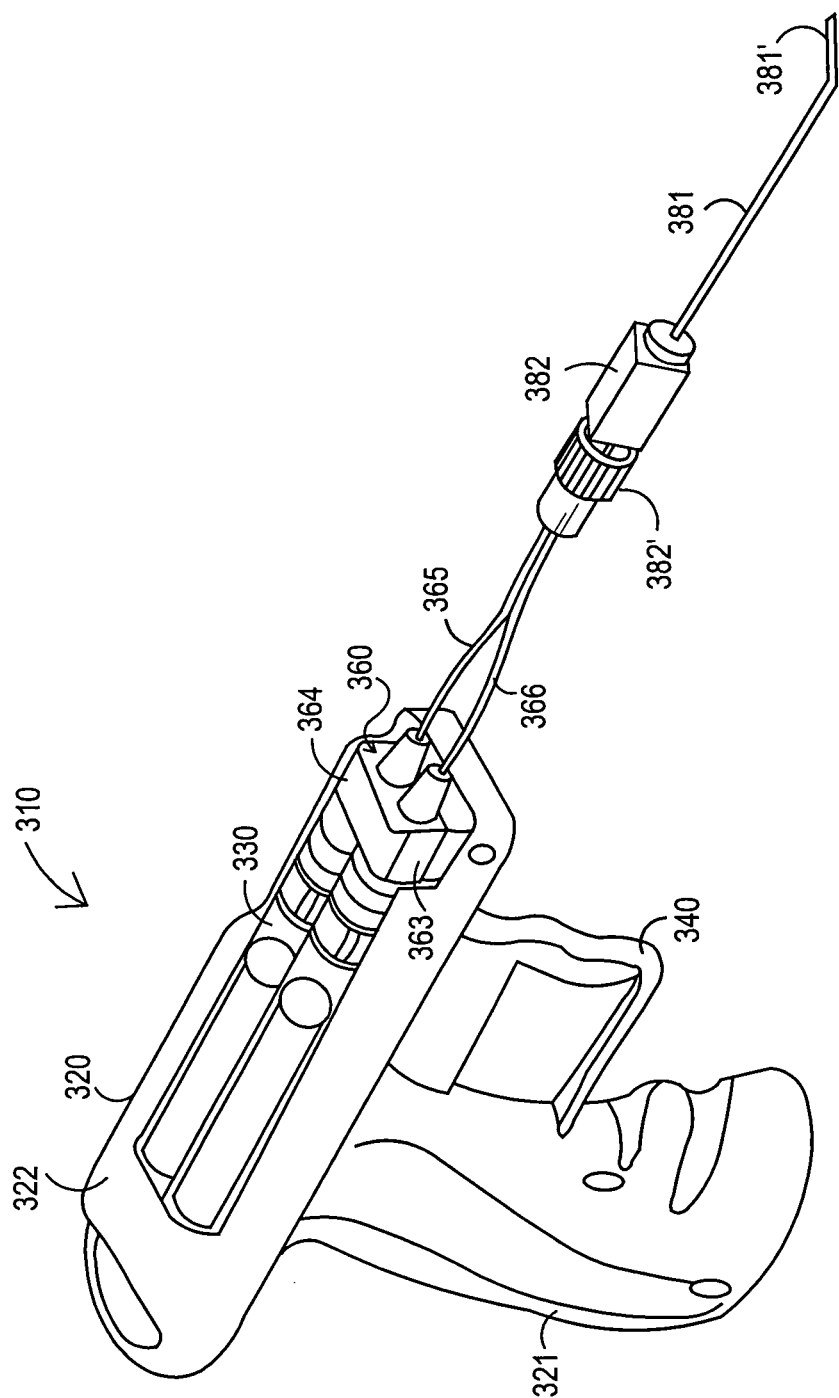
FIG. 12 shows the device of this invention with a delivery manifold operably attached to the device.

A dispenser manifold 360 is shown in FIGS. 4 and 5. The dispenser manifold 360 includes dispenser manifold inlet ports 361, 361' that sealably align and couple with the exit ports 338, 338' of the cartridge 330. The dispenser manifold 360 is adapted to couple to the manifold coupling portion 339 of the cartridge using, for example, fittings 362, 363 that engage complimentary slots 339' so as to lock in the dispenser manifold 360 to the coupling portions 339, 339'. In the embodiment depicted in the FIGS., the exit ports 338, 338' are embodied within manifold coupling portion 339, 339'. The dispenser manifold 360 depicted in FIGS. 4 and 5 also includes an optional hood 364. The dispenser manifold 360 includes fluid tubes 365, 366 that receive and transfer fluid from the cartridge 330 to the needle assembly 380 which is depicted for example in FIGS. 9-11. The tubes 365, 366 can be made of a variety of materials, but in general are made of flexible materials to facilitate improved usage by the surgeon. Typically the tubes 365, 366 are made of polymeric materials, especially medical grade materials. Alternatively, the tubes can be made of soft metals or other materials that permit the tubes to flex. Thus the delivery manifold for delivering the fluids can include a delivery adapter that includes at least two exit ports that each couple to the at least two exit ports of the housing adaptor, at least two conduits having two ends wherein a first end of each of the conduits connects to an exit port of the delivery manifold, and wherein a second end of each of the conduits connects to a duel port luer fittings, wherein the luer fitting is configured to delivery fluid from one conduit to an inner needle and wherein the luer fitting is configured to delivery fluid from the second conduit to a space defined by the exterior of the inner needle and by a second larger diameter needle that connects to the luer fitting with the inner needle being within the insider of the larger diameter needle. FIG. 12 illustrates the device 310 where the manifold 360 has been operably connected to the housing 320 so that the inlet ports of the manifold 360 align with the exit ports of the cartridge 330.

Figure 13:
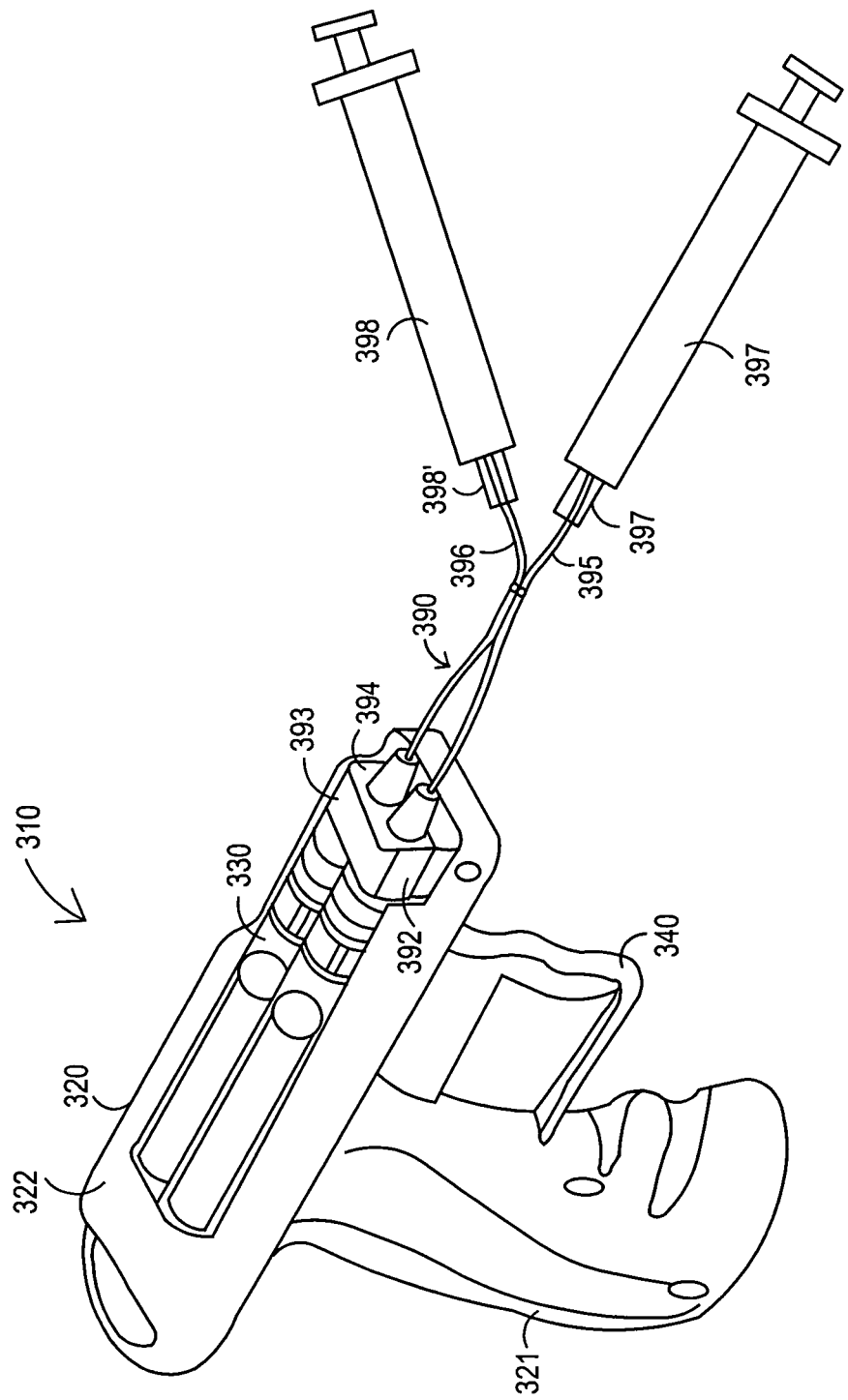
FIG. 13 shows the device of this invention with a fill manifold operably attached to the device.

Instead of the dispenser manifold 360, a fluid fill manifold 390 as depicted in FIG. 13 can be used to load fluids into the cylinders 331, 331' of the cartridge 330. Like the dispenser manifold 360, the fill manifold 390 includes inlet ports (not shown) that sealably align and couple with exit ports 338, 338'. The fill manifold 390 includes fittings 392, 393, and an optional hood 394. However, the fill manifold 390 includes tubes 395, 396 that couple to syringes 397, 398 that are filled with the fluids to be introduced into the cylinders 331, 331'. The syringes 397, 398 connect via luer fittings 397', 398' 399, 399' to the tubes. Thus during use the syringes 397, 398 are filled with fluids (e.g. a thrombin solution and a fibrinogen solution) to be introduced into the cylinders 331, 331'. The syringes are locked into place using the luer fittings, and then the fluids are injected into the cylinders at which time the plungers 336, 336' are driven back. Next, the fill manifold 390 is removed and replaced with the dispenser manifold 360 after which time the surgeon injects the biologic sealant of choice into a desired location, such as a disc, in the body. Thus, the fill manifold for introducing fluids into the cylinder includes a fill manifold adaptor that couples to the adaptor of the delivery device wherein the adaptor includes at least two exit ports that each couple to the at least two exit ports of the housing adaptor, at least two syringes, at least two conduits wherein one end of the conduit connects to the syringe and a second end of the conduit connects to an exit port of the fill manifold adaptor. It should be appreciated that the fill manifold 390 can be alternatively connected to a wide variety of refilling parts other than the syringes 397, 398. Thus, the fluid fill manifold 390 can use, for example, pressurized containers, automated injection devices, fluid bags that are manually or automatically squeezed to effect refilling into the cylinders, fluid ampoules that are punctured with needles to access the fluids using pressurized gas to force the fluids into the cylinders, and so on.

The needle assembly 380 is depicted in FIGS. 9-11. The needle assembly may include two coaxial needles, or an outer needle and an inner polymeric catheter. In FIG. 9, the outer needle 381, which is inserted directly into the patient to be treated, is connected via luer fittings 382, 382' with the outer needle 381 surrounding an inner needle 383 (see FIG. 10). The outer needle is typically an 18-22 gauge spinal needle that includes a bent portion 381' to assist the surgeon in navigating the body during insertion of the spinal needle. The inner needle can be of any size such that fluids may flow in the gap between the needles. In certain embodiments, the inner needle 383 may include ports near the tip 383' to facilitate potentially improved mixing of the fluids. Likewise, the tip 383' may be capped. FIGS. 3A-3C illustrate cross-sectional views of needles and catheters that may be employed in the practice of this invention. If a multi-lumen catheter or needle is employed, then the luer fitting would be adapted to delivery each fluid to a respective lumen. Referring again to FIGS. 9-11, the inner needle 383 can be of any length but typically is sized so that when the inner and outer needles are coupled together the tip 383' of the inner needle 383 extends to within between 1 mm and 50 mm of the tip 381' of the outer needle 381. In one embodiment, a fibrinogen solution is provided to the inner needle 383 while a thrombin solution is provided to the outer needle 381. Fluid mixing is initiated at the tip 383' of inner needle 383.

FIG. 11 shows a detailed embodiment of the luer fitting 382'. Thus, fibrinogen tube 365 feeds fibrinogen solution directly into a port 384 that couples to the inner needle 383. By contrast, tube 364 feeds thrombin solution, for example, into the hub (the void space) 385 of the luer fitting 382' whereby when the outer needle 381 is connected via luer fitting 382 the thrombin solution flows into the hub and into needle 381. The two fluids do not commingle until one of the solutions exits the inner needle 383.

Figure 14:
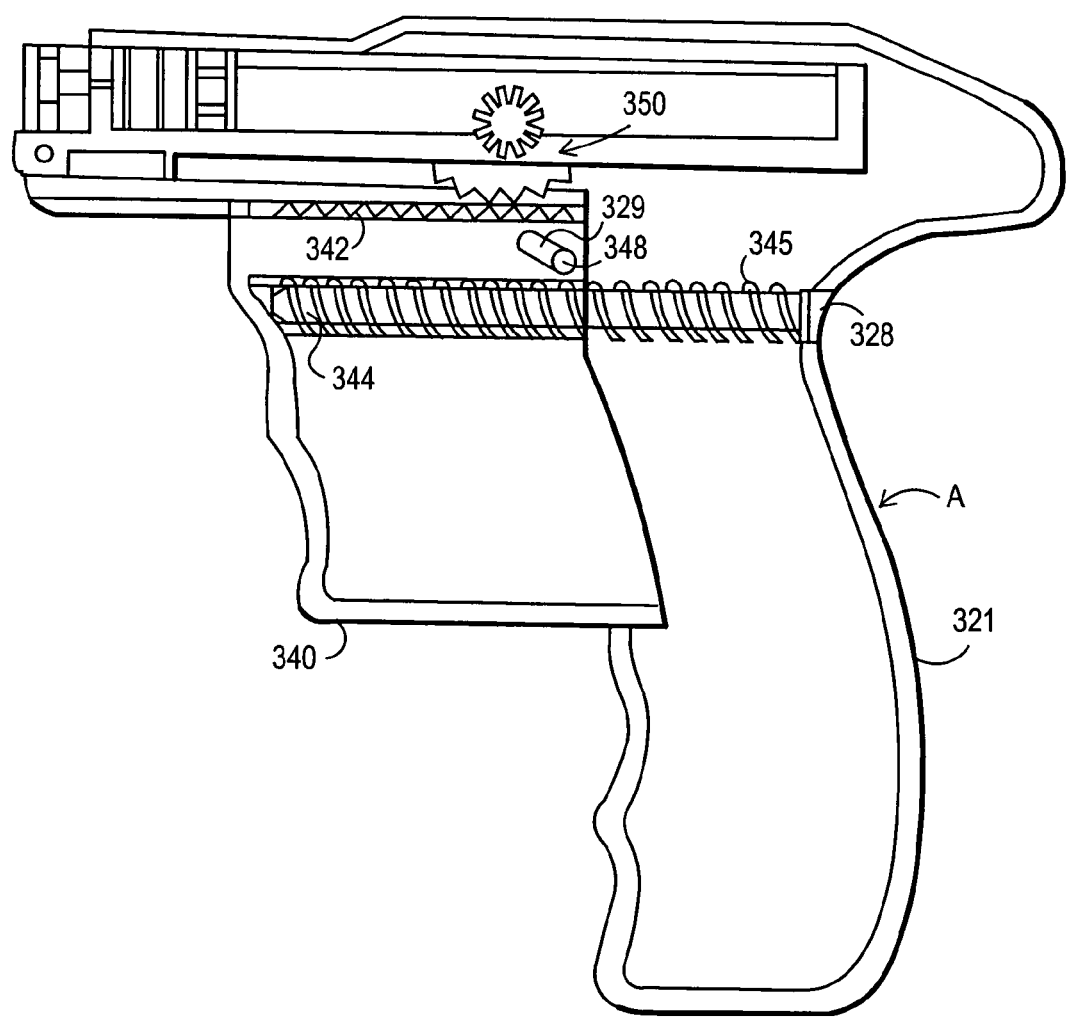
FIG. 14 shows the device of this invention from a cross-sectional view.

The trigger 340 is depicted in greater detail in FIG. 5. The trigger includes a toothed rack 342. Upon application of pressure by the surgeon to the trigger 340, the trigger 340 and rack 342 move backwards in the direction of the handle 321. The rack 342 then engages the wheel assembly 350, which rotates as the rack 342 moves backward. The wheel assembly 350 thereby drives rams 334, 334' which move plungers 336, 336' forward toward the exit ports 338, 338'. In one embodiment, the trigger is configured such that the teeth of rack 342 engage the teeth of the wheel assembly 350 when pressure is applied to the trigger 340, and configured such that the rack 342 drops away when pressure is released so that the respective teeth no longer engage. This configuration can be provided, for example, by adapting the housing 320 and trigger 340 such that the backward motion of the trigger raises the rack 342 such as, for example, in FIG. 14. In FIG. 14, the trigger 340 includes a guide bore 344 wherein a guide post 328 attached to the housing glides through the guide bore 344 upon application of pressure to the trigger 340. Upon release of pressure, spring 345 returns the trigger 340 to its original position. As the trigger 340 slides towards side A of the handle 321, a pin 348 that is mounted or integral with the rack 342 slides in the slot 329 to force the rack 342 up or down depending on the angle of the slot 329 to thereby engage the wheel assembly 350 as pressure is applied to the trigger 340. In this configuration, the slot 329 is a part of and integral with the housing 320. Alternatively, the rack 342 may include a slot with a pin being mounted within the housing 320, such that the pin glides in the slot to force the rack 342 to engage the wheel assembly 350.

Figure 15:
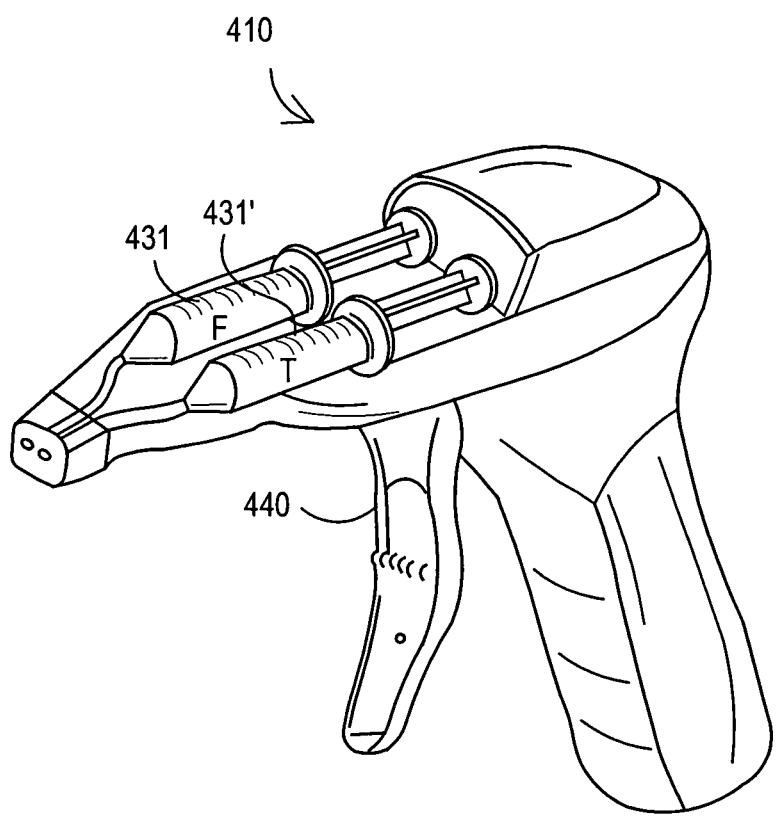
FIG. 15 shows another embodiment of the apparatus of this invention.

FIG. 15 depicts another embodiment of the delivery device of this invention. In FIG. 15, a delivery device 410 is depicted having a different trigger configuration than in, for example, FIG. 4. In FIG. 15, the trigger 440 pivots around a pin, for example, whereby force is applied to the rams to drive the fluid out of the cylinders 431, 431'. One to four squeeze repetitions may be needed to deliver, for example, 4 mL of total fluid. This and other embodiments of this invention can be configured to be force limiting, such as a 100 pounds per square inch maximum and/or 10 pounds per square inch of maximum trigger force. In one embodiment, the ratchet that drives the fluids out of the device will only click once per squeeze, using either locking or non-locking motion. A spring, not shown, returns trigger 440 to its starting position prior to the next squeeze repetition. In this embodiment, the drive system may be the same or different than the wheel assembly 350 discussed above.

Figure 16:
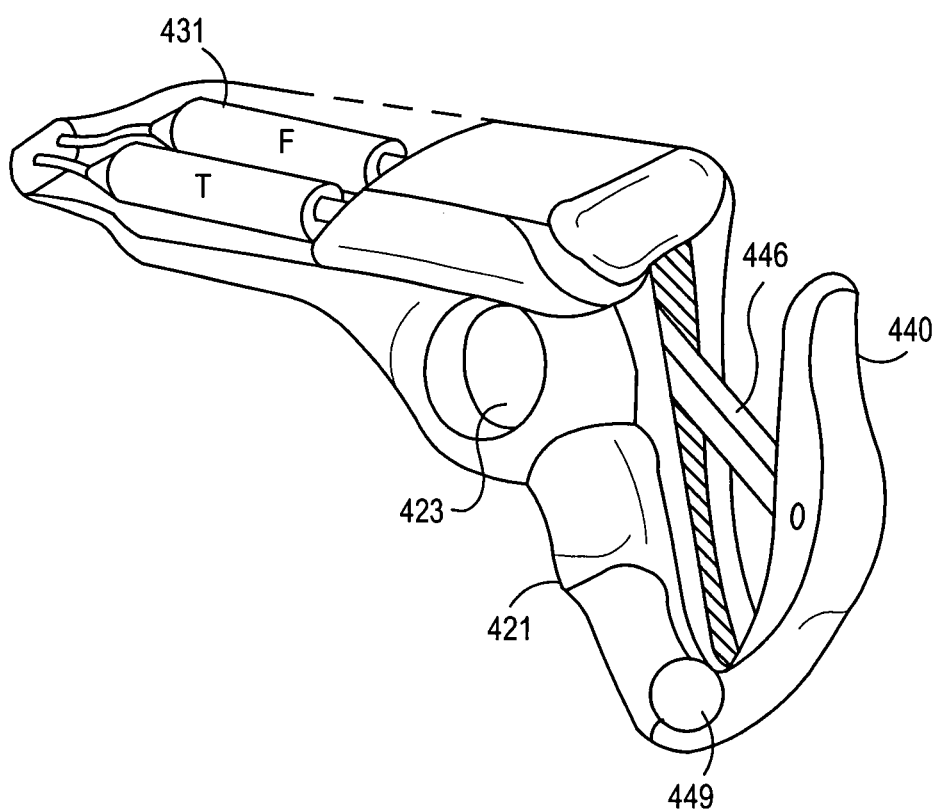
FIGS. 16 and 16A show another embodiment of the apparatus of this invention.
Figure 16A:
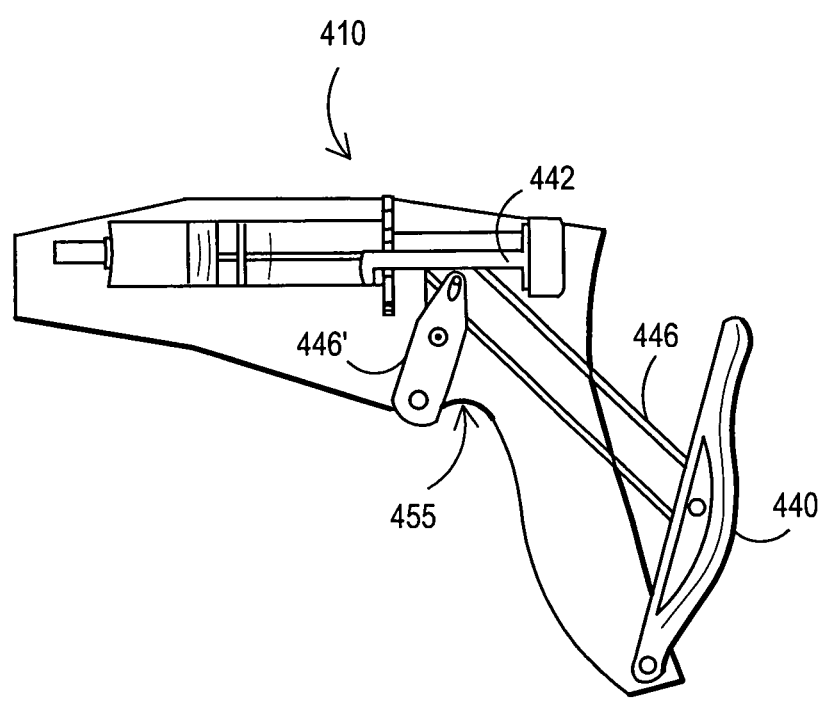

FIG. 16 depicts another embodiment of the invention where the trigger is squeezed on the opposite side of the handle 421 to the fluid reservoirs. In this configuration, the trigger 440 attaches to the handle 421 at pivot point 449. The trigger 440 engages the drive system through drive rod 446. An optional hole 423 is included as part of the housing and handle for placement of at least one finger by the surgeon. In this configuration, the trigger 440 is actuated by direct pressure from the surgeon's palm. The drive assembly can be constructed as in FIG. 16A where application of pressure to the trigger 440 causes the rod 446 to engage a rack 442. The rod 446 can be guided by ratchet arm 446', which may be part of the drive assembly.

Figure 17:
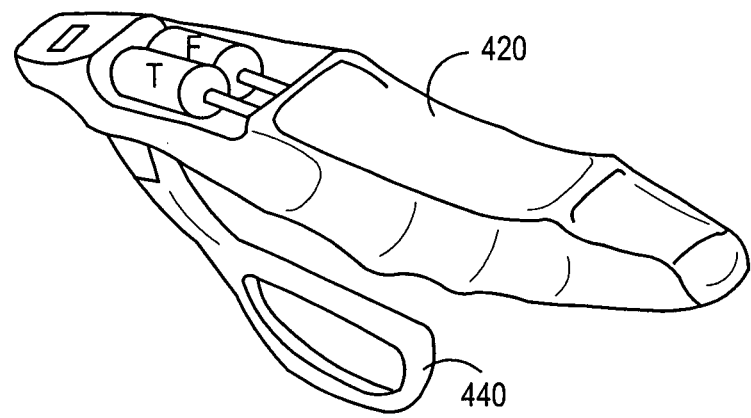
FIGS. 17 and 17A show another embodiment of the apparatus of this invention.
Figure 17A:
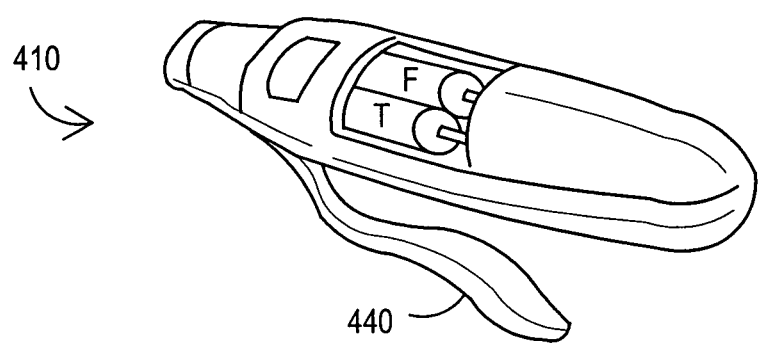

In FIG. 17, device 410 includes an inclined finger loop as the trigger 440. Application of pressure by the surgeon by squeezing the trigger forces the trigger 440 to move toward the housing 420 whereby the drive assembly, not shown, dispenses fluids from the reservoirs. Alternatively, as depicted in FIG. 17A, the trigger does not include a loop.

Figure 18:
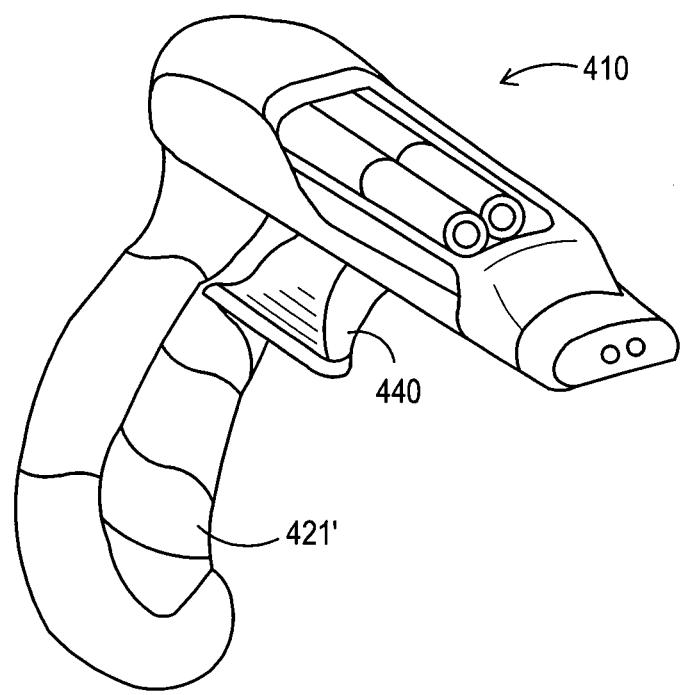
FIG. 18 shows another embodiment of the apparatus of this invention.

In FIG. 18, device 410 includes a soft grip 421' that can be formed from a variety of elastomeric materials or foam. In this configuration, the trigger 440 can be sized for from 1 to 4 finger operation. If desired, a soft grip could provide the surgeon with improved grip or comfort when depressing the trigger. Similarly, the handle can include hatching, ridges, or other the like to improve the grip of the device in the surgeon's hand.

Figure 19C:
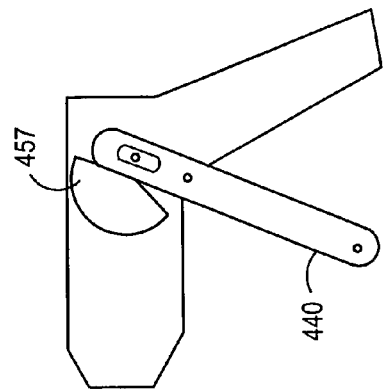
FIGS. 19A-19C show additional embodiments of the apparatus of this invention.
Figure 19A:
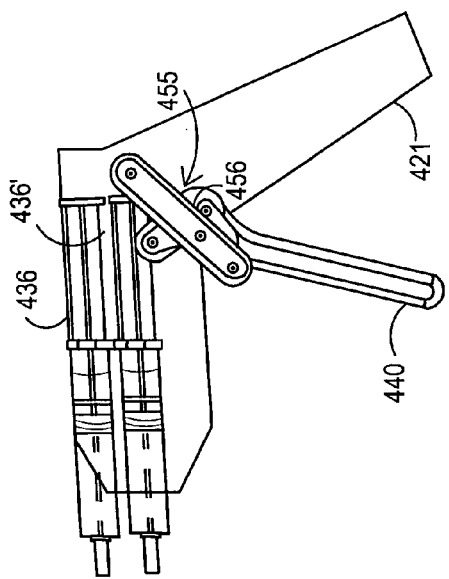
Figure 19B:
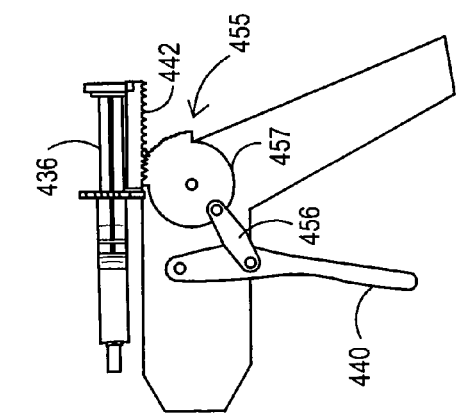

FIGS. 19A and 19B show alternative drive assemblies for use in the practice of this invention. Thus, in FIG. 19A a drive assembly 455 is configured such that the trigger 440 moves through a pivot point that results in the plungers 436, 436' are advanced by application of pressure from the advance rod 456. By contrast, in FIG. 19B the drive assembly is driven by the trigger 440 such that a rod 456 causes a gear 457 to engage a rack 442 to drive the plungers 436, 436'. FIG. 19C illustrates a similar configuration to that in FIG. 19B with an alternative engagement of the trigger 440 to the gear 457.

Figure 20:
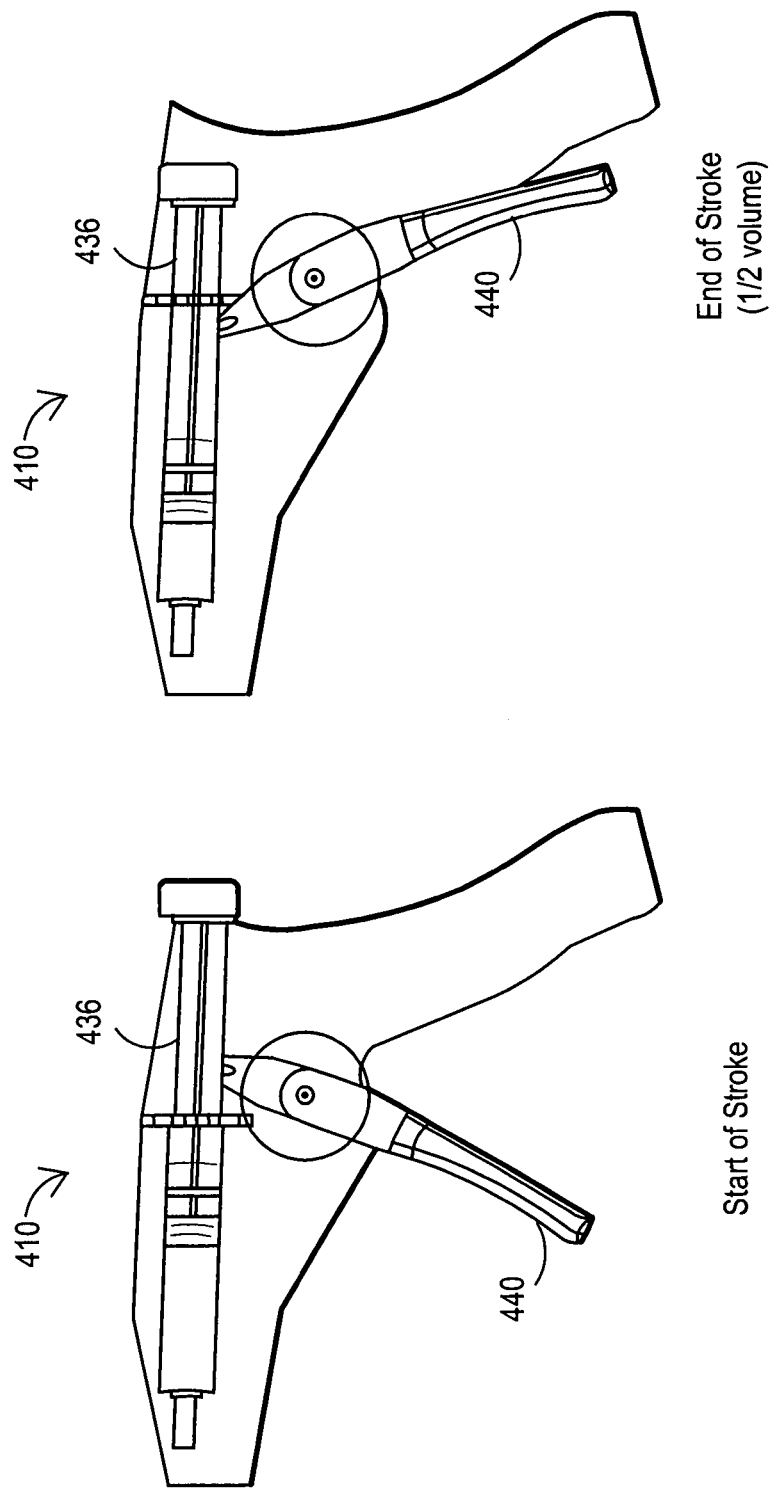
FIG. 20 shows an additional embodiment of the apparatus of this invention during use.

FIG. 20 illustrates a basic ratcheting design where the trigger 440 moves the plunger 436 through a rack (not shown) that engages the plunger 436 as pressure is applied to the trigger 440 by a surgeon by squeezing the trigger. In this configuration, a single repetition will push one-half of the fluid volume out of the reservoirs at the end of the stroke.

Figure 21A:
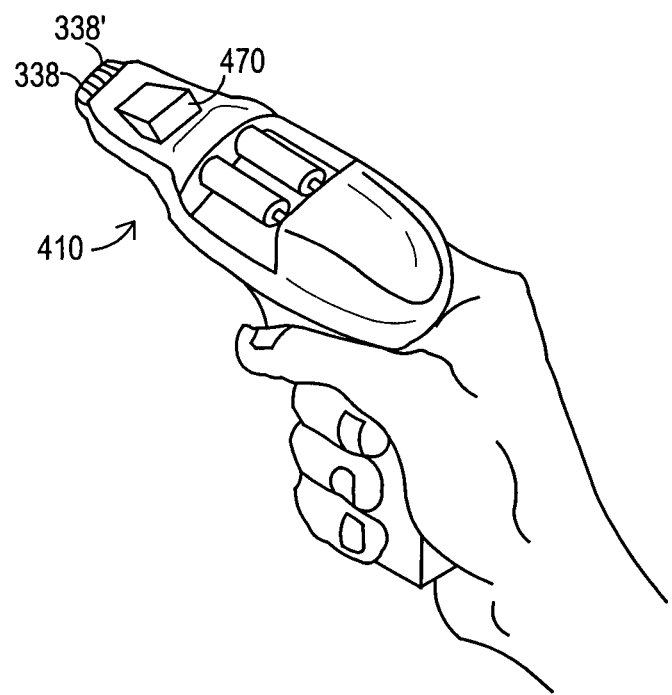
FIGS. 21A-21B show additional embodiments of the pressure display configuration locations.
Figure 21B:
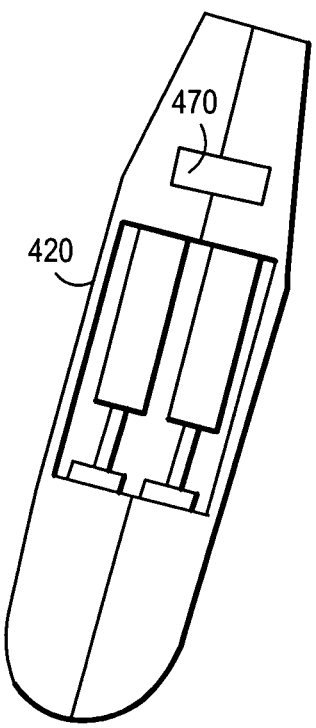

In FIG. 21A an alternative embodiment of the device 410 is shown in which the pressure display is positioned at the front of the device, near the exit ports 38, 38'. In FIG. 21A the display 470 has a raised profile whereas in FIG. 21B the display 470 is mounted flush to the housing 420.

Figure 22B:
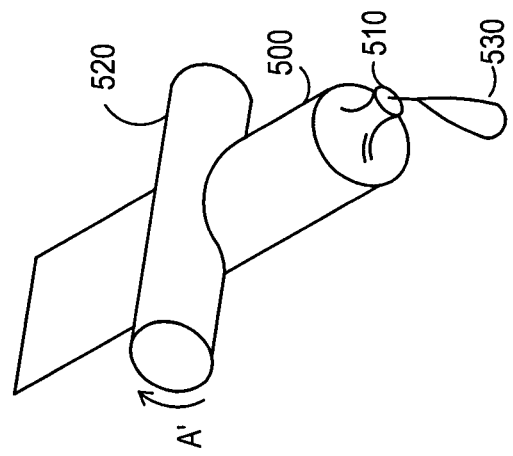
FIGS. 22A and 22B illustrate an alternative embodiment of the fluid delivery reservoirs of this invention.
Figure 22A:
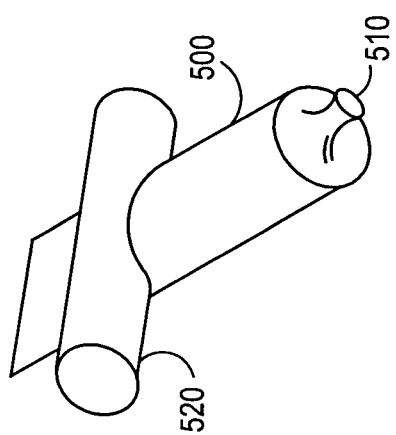

FIGS. 22A and 22B illustrate an alternative embodiment of the fluid delivery reservoirs of this invention. In the embodiment as shown in FIG. 22A the reservoir 500 holds sealant or a component of a sealant. The reservoir includes an exit port 510 for the sealant. A roller 520 It should be appreciated that the roller 520 shown in FIG. 22A is illustrative and can be of a variety of structures that allow application of pressure so that sealant flows from the reservoir 500. For example, the roller 520 could also be in the form of a pair of rollers, or could be a flat structure that simply presses straight down on the reservoir 500. Of course, the device for application of pressure (roller 520 in FIG. 22A) could also be angled or of any configuration that facilitates sealant to be ejected from the reservoir 500. As shown in FIG. 22B, when the roller 520 is rolled in the A' direction, pressure is applied to squeeze sealant 530 out of the reservoir.

The delivery device of this invention can be used to deliver a wide variety of biologic materials (biocompatible sealants, compositions, polymers, and so forth), including pharmaceutical preparations, such as but not limited to fibrin sealant, synthetic polymers such as but not limited to polyvinylpyrrolidone, polyvinyl alcohol, polyacrylic acid, polyethoxazoline, polyhydroxyethyl acrylate, polyhydroxyethyl methacrylate, polysaccharides, polypeptides, polymers made from polyethylene glycol, materials disclosed in U.S. Pat. No. 6,428,576 (Haldimann) which is incorporated herein by reference, and so on, with or without additives. Fibrin sealant is preferred in the practice of this invention. Fibrin sealant comprises a fibrinogen component and a thrombin component that converts fibrinogen to fibrin. The sealant may contain one or more other components. The fibrin sealant is injected into, for example, the disc to seal fissures and tears in the annulus fibrosus. Defects in the annulus fibrosus are commonly diagnosed, currently, using MRI & CT scans and discograms. This can treat both discogenic low back pain and radiculopathy leg pain when injected into the lumbar intervertebral disc.

The fibrinogen used in the practice of this invention includes any fibrinogen that will form fibrin in a human body. Fibrinogen is frequently available in freeze-dried form, and must be reconstituted prior to use. The fibrinogen can also be frozen or fresh. The fibrinogen can be autologous (from the patient to be treated), human including pooled human fibrinogen, recombinant, and bovine or other non-human source such as fish (e.g., salmon and sea trout). The fibrinogen is used in an amount suitable for the given treatment, patient, and so on. The freeze-dried fibrinogen can be reconstituted using, for example, water (for injection), a water solution containing aprotinin (an anti-fibrinolytic agent), a water solution containing calcium ions ($Ca^{+2}$) such as may be supplied from calcium chloride, a water solution containing one or more other additives such as a local anesthetic, saline, a saline solution containing aprotinin, a saline solution containing calcium ions ($Ca^{+2}$) such as may be supplied from calcium chloride, a saline solution containing one or more other additives such as a local anesthetic, or a solution containing combinations of additives.

Thrombin is typically the enzyme used which serves to change fibrinogen to fibrin. However, other enzymes can be used to convert fibrinogen to fibrin, such as those derived from snake venom (e.g., batroxobin), or spider venom as is known in the art. As used herein, "activating compound" refers to a compound that causes fibrinogen to form fibrin, and this term includes thrombin, batroxobin, and so on. Thrombin is available commercially, typically in its freeze-dried form. Freeze-dried thrombin must be reconstituted prior to use. The thrombin can also be frozen or fresh. Thrombin can be recombinant, such as human thrombin (rhThrombin). Thrombin can be autologous, from a human or pooled human supply, bovine, fish (such as salmon) or other non-human fibrinogen-cleaving enzyme source such as various arachnids and other venomous species. The thrombin or enzyme is used in any amount which facilitates changing the fibrinogen to fibrin, as is known to one of skill in the art. The thrombin can be reconstituted using water (for injection), a water solution containing calcium ions, a water solution containing one or more other additives such as a local anesthetic, or a solution containing calcium ions and one or more additives, saline, a saline solution containing calcium ions, a saline solution containing one or more other additives such as a local anesthetic, or a solution containing calcium ions and one or more additives.

Additional additives may be employed in the fibrin sealant such as, but not limited to: antibiotics; antiproliferative, cytotoxic, and antitumor drugs including chemotherapeutic drugs; analgesic; antiangiogen; antibody; antivirals; cytokines; colony stimulating factors; proteins; chemoattractants; EDTA; histamine; antihistamine; erythropoietin; antifungals; antiparasitic agents; non-corticosteroid anti-inflammatory agents; anticoagulants; anesthetics including local anesthetics such as lidocaine and bupivicaine; analgesics; oncology agents; cardiovascular drugs; vitamins and other nutritional supplements; hormones; glycoproteins; fibronectin; peptides including polypeptides and proteins; interferons; cartilage inducing factors; protease inhibitors; vasoconstrictors, vasodilators, demineralized bone or bone morphogenetic proteins; hormones; lipids; carbohydrates; proteoglycans such as aggrecan (chondrotin sulfate and keratan sulfate), versican, decorin, and biglycan; antiangiogenins; antigens; DBM; hyaluronic acid and salts and derivatives thereof; polysaccharides; cellulose compounds such as methyl cellulose, carboxymethyl cellulose, and hydroxy-propylmethyl cellulose and derivatives thereof; antibodies; gene therapy reagents; genetically altered cells, stem cells including mesenchymal stem cells with transforming growth factor, and/or other cells; cell growth factors to promote rehabilitation of damaged tissue and/or growth of new, healthy tissue such as BMP7 and BMP2; type I and II collagen; collagen hydrolysate; elastin; sulfated glycosaminoglycan (sGAG), glucosamine sulfate; pH modifiers; methylsulfonylmethane (MSM); osteogenic compounds; osteoconductive compounds; plasminogen; nucleotides; oligonucleotides; polynucleotides; polymers; osteogenic protein 1 (OP-1 including recombinant OP-1; LMP-1 (Lim Mineralization Protein-1); cartilage including autologous cartilage; oxygen-containing components; enzymes such as, for example, peroxidase, which mediate the release of oxygen from such components; synthetic blood products; melatonin; vitamins; and nutrients such as, for example, glucose or other sugars. However, it is foreseeable that any of these additives may be added to the fibrin sealant separately or in combination. One or more of these additives can be injected with the fibrinogen and activating compound, or alternatively one or more of these components can be injected separately, either before or after the fibrin sealant has been injected.

For solutions containing an incompletely water-soluble additive(s), an anti-caking agent such as, for example, polysorbate, may be added to facilitate suspension of this component. Glycol may be inappropriate for use as an anti-caking agent in the instant invention.

In the practice of this invention, the fibrin sealant is injected into the disc to at least partially repair and/or seal a fissure or fissures in the annulus fibrosus. In particular, fibrinogen and thrombin are injected into the disc, with these components forming fibrin. It should be appreciated that fibrin formation begins immediately on contact of the fibrinogen and thrombin, such as in the Y-connector of a dual syringe or in the needle. The term "injecting" of fibrin sealant as used herein thus encompasses any injection of components that form fibrin in the disc, including circumstances where a portion of the components react to form fibrin due to mixing prior to contact with or actual introduction into the disc.

It should also be appreciated that the point, or points, of injection (e.g., at the tip of a spinal needle) can be within the annulus fibrosus, on the outer surface of the anulus fibrosus or in the nucleus pulposus. If the injection occurs in the nucleus pulposus, the injected components may form a patch at the interface between the nucleus pulposus and the annulus fibrosus, or, more commonly, the components flow into the defect(s) (e.g., fissures) of the annulus fibrosus and potentially "overflowing" into the interdiscal space. In practice, over-pressurizing the disc by injecting the components into the disc should be avoided.

The fibrinogen and activating compound are injected in amounts effective to seal a given defect of the disc, as is apparent to one of skill in the art. The amount of activating compound such as thrombin can be varied to reduce or lengthen the time to complete fibrin formation. In general, the higher level of thrombin per unit amount of fibrinogen, the faster fibrin formation occurs. If slower fibrin formation is desired, then less thrombin is used per unit fibrinogen. The use of calcium ions (such as from calcium chloride) in one or both of the component solutions will affect the strength of the fibrin so formed, with increasing amount of calcium ions increasing the strength of the fibrin clot. Generally, for a composition comprising fibrinogen that is an aqueous solution, it is believed that from about 3 mL to about 5 mL of such composition is sufficient to be an effective fibrin sealant. However, depending on the use of the composition, the dosage can range from about 0.05 mL to about 40 mL.

Fibrin sealants mimic the final stage of the natural clotting mechanism. Typically, such sealants entail the mixing of a fibrinogen component with an activating enzyme such as thrombin. Thrombin is an enzyme that exists in blood plasma which causes the clotting of blood by converting fibrinogen into fibrin. In normal practice, some commercially available components of the fibrin sealant are reconstituted separately, from a freeze-dried state, prior to use. However, the use of samples prepared from a frozen state or a fresh state is also acceptable. To increase biocompatibility of the sealant with host tissue, various components may be supplied endogenously from host body fluids. Combining the reconstituted components produces a viscous solution that quickly sets into an elastic coagulum. A method of preparing a conventional fibrin sealant is described by J. Rousou, et al. in Journal of Thoracic and Cardiovascular Surgery, vol. 97, no. 2, pp 194-203, February 1989. Cryoprecipitate derived from source plasma is washed, dissolved in buffer solution, filtered and freeze-dried. The freeze-dried fibrinogen is reconstituted in a fibrinolysis inhibitor solution containing, for example 3000 KIU/ml of aprotinin (a polyvalent protease inhibitor which prevents premature degradation of the formed fibrin). The solution is stirred and heated to a temperature of about 37° C. Each solution (the thrombin and fibrinogen solutions) is drawn up in a dual barrel syringe and mounted on a Y-connector to which a needle is attached for delivery of the combined solution. (See, e.g. the Duploject® device, from ImmunoAG, Vienna, Austria). Thus, mixing of the components only occurs during the delivery process which facilitates clot formation at the desired site of application only. The components should be injected sufficiently quickly to avoid the passage becoming blocked due to fibrin formation in the needle.

Calcium ions may be included in the fibrin sealant to be injected to modify the composition of the so-formed fibrin and resulting strength of the clot.

In one embodiment, about 75-105 mg/mL of freeze-dried fibrinogen is reconstituted according to conventional methods, and about 45-55 mg/mL thrombin component is reconstituted separately from a freeze-dried state according to the methods and compositions of the present invention. Freeze-dried fibrinogen and freeze-dried thrombin are available in kit-form from such manufacturers as Baxter under names such as TISEEL®. These two fibrin sealant components can be prepared for example in about 2 mL samples each to yield approximately 4 mL of total sealant (reconstituted fibrinogen plus reconstituted thrombin).

While several methods and compositions may be used for preparing the freeze-dried thrombin for use in the invented fibrin sealant, one method is providing about 45-55 mg/mL of freeze-dried thrombin and mixing it with a reconstituting solution. The reconstituting solution may optionally further comprise about 0.1-100 milligrams of another additive described herein (e.g., local anesthetic) and/or calcium ions. The calcium ion solution (e.g.: calcium chloride) concentration can be, for example, 1-100 millimoles/mL, and in one embodiment 4-40 millimoles/mL. If employed, the calcium+ ion concentration should be sufficient to further the polymerization reaction that forms a durable fibrin sealant clot. A preservative-free reconstituting solution may be desirable, but is not required.

A contrast agent may be used in conjunction with the injection of the fibrin sealant. The contrast agent may be injected prior to injection of the fibrin sealant. Alternatively, the contrast agent is included in the fibrinogen component or thrombin component that is injected into the disc. Contrast agents and their use are well known to one of skill in the art.

Alternative amounts and concentrations of fibrinogen and thrombin may be used to form the desired fibrin sealant clot in the body. For example, as discussed above, varying the fibrinogen and/or thrombin amount/concentration may be done to vary the viscosity and the "setting time" of the combined fibrinogen and thrombin components. Likewise, varying fibrinogen may change the density of the combined components, which may be important for controlling flow through a long conduit such as a catheter into the body. Varying thrombin may vary the polymerization time of the components, which may be important for controlling the time at which the clot forms for ensuring the components set-up at the proper site and time in the body rather than setting-up prematurely.

When acquired in freeze-dried form, the thrombin and fibrinogen need to be reconstituted for use. The thrombin reconstituting solution (e.g., a sterile water-based CaCl solution), optionally containing one or more additives, can be prepared in a single vial prior to mixing with the freeze-dried thrombin. This component of the fibrin sealant may then be provided to users in a reconstituted state, or in two uncombined vials containing freeze-dried thrombin and a premixed reconstitution solution. Mixing of the contents of the two vials may be performed at any point up to, and including, the time at which the fibrin sealant (or its components) is injected into the patient. Reconstitution of the fibrinogen solution can be accomplished according to conventional methods. For example, the fibrinogen component may be reconstituted in a sterile water solution which optionally contains additives such as, for example, aprotinin, a local anesthetic. If desired, the thrombin or the fibrinogen or both can be reconstituted using a sterile water solution that contains one or more additives. All solutions are brought to a temperature of about 37° C. Preferably, the thrombin is combined with the fibrinogen solution using the dual-syringe injection procedure described herein to form a single sealant composition which is injected into a patient. The instant invention provides a vehicle for the delivery of the sealant that conveys the sealant to the precise area of the back, seals any annular fissures, and holds the fibrin in place via the elastic coagulum. In addition, the biodegradable nature of the formed fibrin clot minimizes or eliminates the need for invasive surgical removal following the effective period of use. Therefore, an advantage of the sealant and method of application is the ability to provide a minimally invasive means of accomplishing localized, prolonged sealing of defects (e.g., fissures) in the annulus fibrosus, and if an additive is in the sealant, time-released additive delivery.

In general, the fibrin sealant of this invention is injected into the disc, the epidural space, the zygapophysial (2-joint) joint, the lateral atlanto-axial joint, the vertebral canal, and/or thecal sac. With respect to an injection of fibrin sealant into a disc, an intra-discal injection serves to create a fibrin matrix which seals the disc from leaking material from the nucleus into the area outside the disc. Alternately, this treatment may insulate innervated granular tissue from the effects of nucleus pulposus. The presence of this innervated granular tissue sometimes found within the annulus at the site of an anular defect or tear, is believed to be a common physiologic healing response. For example, the fibrin sealant can be delivered by fluoroscopic transforaminal lumber epidural or intra-discal injection, such as described in U.S. Pat. No. 6,468,527. For the treatment of back injuries such as these, the fibrin sealant is injected into the nucleus pulposus, to fill any fissures or voids of the annulus fibrosus, to seal the bone end plates to the disc, increase pressure of the disc, and to increase the height of the disc space. In general, the fibrin sealant is injected at a location near the defect in the annulus fibrosus. Typically the fibrin sealant will flow into the fissures in the annulus fibrosus, and some fibrin sealant may thus flow out of the intra-discal space. The injection may also serve to coat areas adjacent to the disc, directly on the nerve roots and surrounding areas which serve to protect those areas from the effects of the leaking nucleus material. Sealing the fissures and bone end plates halts the leakage of harmful chemicals into the disc environment and prevents the initiation of foreign-body reactions towards the damaged disc by the immune system. Increasing the disc space relieves pressure on the nerve root. That is, as a result of the injection, an increase of the disc height occurs, which increases the spacing between lamina, and which in turn relieves pressure on the nerve roots on the lamina. For this application, supplementation of the fibrin sealant with growth factors may promote rehabilitation of the damaged tissues or the gradual replacement of the fibrin sealant with healthy tissue.

With respect to treatment of a disc, an introducer needle is inserted into the intra-discal space with the tip being positioned close to the defect in the annulus fibrosus. A finer gauge fluid delivery tube such as a needle or catheter is then inserted into the introducer needle. The fibrin sealant is injected through the fluid delivery tube. With either a finer gauge needle or a catheter made for instance of synthetic polymer, the needle or catheter can be advanced through the introducer needle and into the nucleus pulposus. Alternatively, the needle or catheter can be advanced up to the tip of the introducer needle, but not far as to go beyond the tip of the introducer needle. In one embodiment, the fluid delivery tube has a tip that extends no more than 1 mm from the tip of the introducer needle and no less than 10 mm from the tip of the introducer needle so that mixing of fibrin sealant injected through the fluid delivery tube and the introducer needle at least partially occurs in the introducer needle. In another embodiment, the fluid delivery tube includes a plurality of holes toward the distal tip that permits fluid to exit the fluid delivery tube prior to the distal tip. In another embodiment, the fluid delivery tube is of a length such that during use the fluid delivery tube extends within the introducer needle into the intra-discal space of a human disc, and wherein the fluid delivery tube is of a length such that fluid injected through the fluid delivery tube first contacts fluid injected through the introducer needle within the bore of the introducer needle. In another embodiment, the fluid delivery tube has a tip that extends no more than 1 mm from the tip of the introducer needle. In one embodiment, the fluid delivery tube has a tip that extends no more than 1 mm from the tip of the introducer needle so that mixing of fibrin sealant injected through the spinal needle and the introducer needle at least partially occurs in the introducer needle. In another embodiment, the fluid delivery tube has a tip that extends no more than 1 mm from the tip of the introducer needle and no less than 5 mm from the tip of the introducer needle so that mixing of fibrin sealant injected through the fluid delivery tube and the introducer needle at least partially occurs in the introducer needle. This invention has the advantage of precisely positioning the point of injection, particularly since a polymeric catheter could bend in the nucleus pulposus thereby becoming mispositioned. Likewise by positioning the introducer needle at the desired point of injection as an initial matter, the fibrin sealant can be injected quickly to expedite the procedure, which is a benefit to the patient.

The gap between the tip of the catheter and the tip of the needle facilitates mixing of the fibrinogen and the thrombin prior to these components exiting the introducer needle. A standard introducer needle of gauge 16 to 22 or in another embodiment 18 to 22 can be employed. Alternatively, the needle can be adapted to increase mixing of the components. For example, the internal surface of the needle can be scored or otherwise textured to assist in the mixing of the components. Also, the tip of the needle can be diminished in size relative to the balance of the needle. This may be referred to as "necking down" the tip of the needle. The necked down needle can be made in a number of ways, including during production of the needle by drawing the tip out, or by attaching a thinner gauge needle to the tip of the introducer needle such as by use of a swaging technique. Alternatively, some other means of increasing static mixing of the components can be employed.

Use of the improved fibrin sealant composition may be better understood by reference to the following example. These examples are representative and should not be construed to limit the scope of this invention or claims hereof.

Example 1

Fluoroscopic Guided Intra-Discal Injection

After sterile preparation, an introducer needle is advanced in oblique projection to a superior articular process. A curved spinal needle is advanced through the introducer needle into the disc. Both anterior-posterior and lateral fluoroscopic projections are used to confirm proper needle placement. If the needle placement needs to be adjusted, placement is again confirmed fluoroscopically. A contrast agent is injected to confirm needle placement. In patients with chemical radiculitis, the contrast agent can be observed to be leaking through the annular fissures and/or intra-discal pathology, thus permitting their identification. Once the needle is properly positioned in the intra-discal space, the fibrin sealant (or its components) is injected using the syringe system of this invention. Pressure can be optionally monitored to ensure that the disc is not over-pressurized. The fibrin sealant is observed to force the contrast agent from the intra-discal space as it seals the annual fissures. Alternatively, the contrast agent is injected with the sealant. Alternatively, no contrast agent is used. The procedure seals the defects/fissures of the annulus fibrosus and stops the chemical leakage and facilitates regeneration within the disc.

It is envisioned that the present invention may be used to address various conditions through use of the fibrin sealant in a manner similar to that described in the examples above. Discussion of this invention referenced particular means, materials and embodiments elaborating limited application of the claimed invention. The invention is not limited to these particulars and applies to all equivalents. Although this invention has been described above with reference to particular means, materials and embodiments, it is to be understood that the invention is not limited to these disclosed particulars, but extends instead to all equivalents within the scope of the following claims.

What is claimed is:

1. A method of percutaneously treating a disc that is leaking nucleus pulposus into or through at least one defect in the annulus fibrosus, comprising:
    advancing a hypodermic needle through skin percutaneously, through the annulus fibrosus and into the nucleus pulposus by piercing the skin, the annulus fibrosus and the nucleus pulposus with the hypodermic needle, wherein the hypodermic needle can be attached to a connector and the hypodermic needle has a distal tip;
    inserting a fluid delivery tube into the hypodermic needle up to but not beyond the distal tip of the hypodermic needle;
    wherein the fluid delivery tube has a distal tip and is configured so that the distal tip of the fluid delivery tube does not extend past the distal tip of the hypodermic needle;
    injecting components of a biologic sealant that begin mixing after the connector and within the space between the distal tip of the hypodermic needle and the distal tip of the fluid delivery tube.

2. The method of claim 1, wherein the fluid delivery tube is a multilumen catheter.

3. The method of claim 1, wherein the fluid delivery tube is a second needle, wherein a fibrinogen solution passes through and in direct contact with the hypodermic needle and wherein an activating solution passes through and in direct contact with the second needle.

4. The method of claim 1, wherein the fluid delivery tube is a second needle, wherein an activating solution passes through the hypodermic needle and wherein a fibrinogen solution passes through the second needle.

5. The method of claim 1, wherein the biologic sealant is fibrin sealant, and wherein calcium ions are injected with the fibrin sealant.

6. The method of claim 1, further comprising measuring the pressure of one component while the components are being injected.

7. The method of claim 1, wherein an additive is injected with the fibrinogen and the activating compound, wherein the additive is selected from the group consisting of antibiotics; antiproliferative, cytotoxic, and antitumor drugs including chemotherapeutic drugs; analgesic; antiangiogen; antibody; antivirals; cytokines; colony stimulating factors; proteins; chemoattractants; EDTA; histamine; antihistamine; erythropoietin; antifungals; antiparasitic agents; non-corticosteroid anti-inflammatory agents; anticoagulants; anesthetics; analgesics; oncology agents; cardiovascular drugs; glycoproteins; fibronectin; peptides including polypeptides and proteins; interferons; cartilage inducing factors; protease inhibitors; vasoconstrictors, vasodilators, demineralized bone or bone morphogenetic proteins; hormones; lipids; carbohydrates; proteoglycans; antiangiogenins; antigens; DBM; hyaluronic acid and salts and derivatives thereof; polysaccharides; cellulose compounds and derivatives thereof; gene therapy reagents; genetically altered cells, stem cells including mesenchymal stem cells with transforming growth factor, and/or other cells; cell growth factors; type I and II collagen; collagen hydrolysate; elastin; sulfated glycosaminoglycan (sGAG), glucosamine sulfate; pH modifiers; methylsulfonylmethane (MSM); osteogenic compounds; osteoconductive compounds; plasminogen; nucleotides; oligonucleotides; polynucleotides; polymers; osteogenic protein 1 (OP-1 including recombinant OP-1); LMP-1 (Lim Mineralization Protein-1); cartilage; oxygen-containing components; enzymes; melatonin; vitamins; nutrients; and combinations thereof.

8. The method of claim 1, wherein the at least one defect is a tear or fissure in the annulus fibrosus.

9. The method of claim 1, wherein normal physiologic hydrostatic pressure in the disc is restored or normal disc height is restored or both.

10. The method of claim 1, wherein the biologic sealant is fibrin sealant that includes a fibrinogen component and the fibrinogen of the fibrin sealant is autologous.

11. The method of claim 1, wherein the injection is performed using a dual barrel syringe.

12. The method of claim 1, wherein the disc is a lumbar disc.

13. The method of claim 1, wherein the disc is a thoracic disc.

14. The method of claim 1, wherein the disc is a cervical disc.

15. The method of claim 1, wherein a contrast agent is injected either before, with, or after the components of the biologic sealant have been injected.

16. The method of claim 1, wherein a local anesthetic is injected into the disc.

17. The method of claim 1, wherein the fluid delivery tube is a bilumen catheter.

18. The method of claim 1, wherein the fluid delivery tube is a trilumen catheter.

19. The method of claim 1, wherein two flexible tubes are connected to the connector, wherein each component of the biologic sealant flow through opposite flexible tubes to transmit the components to the hypodermic needle and the fluid delivery tube while injecting the components.

20. The method of claim 1, wherein after the hypodermic needle is advanced into the nucleus pulposus and the fluid delivery tube is inserted, the distal tips of hypodermic needle and the fluid delivery tube both extend past the annulus fibrosus.

21. The method of 1, wherein the hypodermic needle is at least 5 inches long.

* * * * *